US005695954A

United States Patent [19]
Sherwood et al.

[11] Patent Number: 5,695,954
[45] Date of Patent: Dec. 9, 1997

[54] DNA ENCODING TWO FISH NEUROPEPTIDES

[75] Inventors: Nancy Gail McKeown Sherwood; David Bernard Parker; John Edwin McRory; David William Lescheid, all of Victoria, Canada

[73] Assignee: University of Victoria Innovation & Development Corporation, Victoria, Canada

[21] Appl. No.: 62,472

[22] Filed: May 14, 1993

[51] Int. Cl.$^6$ ............................ C12N 15/16; C12N 15/12; C12N 15/85; C12N 5/10
[52] U.S. Cl. ............... 435/69.1; 435/69.2; 435/69.4; 435/252.3; 435/325; 435/365.1; 435/320.1; 536/23.1; 536/23.51; 935/11
[58] Field of Search .................... 536/23.1, 23.5, 536/23.51; 435/69.1, 69.4, 70.1, 70.3, 71.1, 240.2, 172.1, 243, 7.21, 252.3, 325, 365.1, 320.1, 69.2; 530/324; 514/12; 935/9, 11

[56] References Cited

U.S. PATENT DOCUMENTS

| 5,128,242 | 7/1992 | Arimura et al. | 435/7.21 |
| 5,326,860 | 7/1994 | Onda et al. | 530/324 |

FOREIGN PATENT DOCUMENTS 0404034  12/1990  European Pat. Off. .

OTHER PUBLICATIONS

Harvey, S., and Scanes, Colin G. Comparative stimulation of growth hormone secretion in anaesthetized chickens by human pancreatic growth hormone-releasing factor (hpGRF) and thyrotrophin-releasing hormone (TRH). Neuroendocrinology 39: 314–320 (1984).

Harvey, S. Thyrotrophin-releasing hormone: a growth hormone-releasing factor. J. of Endocrinology 125: 345–358 (1990).

J. M. Vaughan et al., "Isolation and characterization of hypothalamic growth-hormone releasing factor from common carp, *Cyprinus carpio*", Neuroendocrinology 56: 539–549 (1992).

D. B. Parker et al., "Evidence of a growth hormone-releasing hormone-like molecule in salmon brain, *Oncorynchus keta* and *O. kisutch*", Gen. Comp. Endocrinol. 79: 95–102 (1990).

S. Marivoet et al., "Localization of growth hormone releasing factor-like immunoreactivity in the hypothalamo-hypophyseal system of the frog (*Rana temporia*) and the sea bass (*Dicentrarchus labrax*)", Gen. Comp. Endocrinol. 72: 72–79 (1988).

S. Ohkubo et al., "Primary structure and characterization of the precursor to human pituitary adenylate cyclase activating polypeptide", DNA Cell Biol. 11: 21–30 (1992).

D. B. Parker et al., "Two salmon neuropeptides encoded by one brain cDNA are structurally related to members of the glucagon superfamily", Eur. J. Biochem. 215: 439–448 (1993).

Ogi, K., et al., "Molecular Cloning and Characterization of cDNA for the Precursor of Rat Pituitary Adenylate Cyclase Activating Polypeptide (PACAP)", Biochem. and Biophys. Research Comm. vol. 173 3:1271 (1990).

Kimura, C. et al., "A Novel Peptide which Stimulates Adenylate Cyclase: Molecular Cloning and Characterization of the Ovine and Human cDNAs", Biochem. and Biophys. Research Comm. vol. 166 1:81 (1990).

Rivier, J., et al., "Characterization of a Growth Hormone-Releasing Factor from a Human Pancreatic Islet Tumor", Nature 300:276 (1982).

Guillemin, R., et al., "Growth Hormone-Releasing Factor from a Human Pancreatic Tumor that Caused Acromegaly", Science 218:585 (1982).

Spiess, J., et al., "Characterization of Rat Hypothalamic Growth Hormone-Releasing Factor", Nature 303:532 (1983).

Baringa, M., et al., "Transcriptional regulation of Growth Hormone Gene Expression by Growth Hormone-Releasing Factor", Nature 306:84 (1983).

Frawley, L.S., and Hoeffle, J.P., "Hypothalamic Peptides Affect the Ratios of GH and PRL Cells: Role of Cell Division", Peptides 9:825 (1988).

Gick, G.G., et al., "Growth-Hormone-Releasing Factor regulates Growth Hormone mRNA in primary Cultures of Rat Pituitary Cells", PNAS (USA) 81:1553 (1984).

Guillemin, R., "Hypothalamic Control of Pituitary Functions. The Growth Hormone Releasing Factor", Liverpool University Press, Liverpool, UK pp. 1–73 (1986).

Frohman, L.A. and Jansson, J.O., "Growth Hormone-Releasing Hormone", Endocr. Rev. 7:223 (1986).

Mayo et al PNAS 82 63–67 (1985).

Frohman et al Mol. Endocrinol. 3 1529–36 (1989).

Ackland et al Peptides 10 15–19 (1989).

Friedenreich et al Nuc Acids Res. 18 3299–3305 (1990).

*Primary Examiner*—Paula K. Hutzell
*Assistant Examiner*—Robert C. Hayes
*Attorney, Agent, or Firm*—Klarquist, Sparkman, Campbell, Leigh & Whinston, LLP

[57] ABSTRACT

Novel DNAs are provided which code for fish PACAP and GHRH-like peptide. Methods are provided for production of fish PACAP and fish GHRH-like peptide by expression of the novel DNAs. Additionally, methods are provided for producing enhanced growth of fish by transfection with the novel DNAs of the invention. Further a method is provided for identification of transgenic fish.

27 Claims, 21 Drawing Sheets

Figure 1

```
-321
     gacgaatctcatcgacaatttttttttgttcgcagaaggctattatttttcattgttgttttttagaag
     cggcttattgtataaaagtcaaaggcggctctctctctctcctcaggacgagaccatcaggaatatcggcggctcagagaaagag
     gtgccgagagaaagattacctcgtctctctctctctctctctccctctctcctctgtgctggtggctctctttcactcacac
     atacacacatagacacacacacacacgctctcagcagccgagccgcaccgagcccgaagcccgctccgcagccgcctcctcctgaccaaactgcc
     gtagc +1   atg gcc aaa tct agt aga gct act ttg gct ctg ctc atc ctc ggg atc tta atg cgc tac    60
     Met ala lys ser arg ala thr leu ala leu ile leu gly ile leu met arg tyr
                                    10                                    20 agc caa tgc aca ccc atc gga atg ggc ttc ccc aat atg agg cta gac aac gac gtg ttc   120
     ser gln cys thr pro ile gly met gly phe pro asn met arg leu asp asn asp val phe
                   30                                    40 ggg gac gag gga aac tcg tta agt gag ctg tcc tac gag ccg gac acg atg agc gcg cgc   180
     gly asp glu gly asn ser leu ser glu leu ser tyr glu pro asp thr met ser ala arg
                   50                                    60 agt cgt cca gcc ctc cct gaa gac gca tac aca ctg tat tyr ccg ccc gag aga aga gcc   240
     ser arg pro ala leu pro glu asp ala tyr thr leu tyr tyr pro pro glu arg arg ala
                   70                                    80 gaa acg cat gca gac gga tta gat aga gcc ttg agg gac atc ctg gtt cag tta tca      300
     glu thr his ala asp gly leu asp arg ala leu arg asp ile leu val gln leu ser
                   90                                   100 gcc cga aaa tat ctg cat tct ctg acg gca gtt cgc gta ggt gag gaa gaa gag gat gaa   360
     ala arg lys tyr leu his ser leu thr ala val arg val gly glu glu glu glu asp glu
                  110                                   120 gag gac tcg gag cca ctg tcg aag cgc cac tcg gac ggc att gga ttc acg gac agc tac tcg 420
     glu asp ser glu pro leu ser lys arg his ser asp gly ile phe thr asp ser tyr ser
                  130                                   140 cgc tac cgg aaa caa atg gcc gta aaa ata cct tgc agc agt gct ggg aag aag gta       480
     arg tyr arg lys gln met ala val lys ile pro cys ser ser ala gly lys lys val
                  150                                   160 cag aca gag att tag aaa caa agg acg gcg ctt ggt tgt acc atc agt ttg gac cat       540
     gln thr glu ile     lys gln arg thr ala leu gly cys thr ile ser leu asp gly his tag ggacactgtcataatcactccggagagagaggaaaaaggtattaagagtgcctgctcccaggtcacgtctctgt
     ***
```

Figure 2a

```
gaagtgaacaagcagttgaatgaacccatgtgtgattgctcattctgatgtcctgagacaccaaattggtgtcaaagat
tggtgaggttgtgcagaatctgtattccagaatgattcatctgcttgagcttggtcatcgtgtcaaggacttccatcttaact
tgcaagcatggttgagcctgcaactattaagttgcatcagctgctgctgcttactctgcctgaactctgaactccatcttaact
atggagatgaaattgactaaaggatgaggattctgtgtatccagcgatgttgatttgtcaaatgagactgaaaaggct
ggtgtagaggacagaatctcctacgcacttcttcaaggcatgtgagtgactgccagagagagcgatccctctcagcat
ggagattatgtgcctctgtacaacgacaccagagttcttgcattgaccaacagaattgcttcctgaggaaagccagagt
tgcattaaactggggtatagatcaagcaactctgccattgaccaacagaattgcttcctgaggaaagccaagttgtagtt
agtactactgaaaaactgaaactgatgagttttgttaacttggccgaattaaggctggagtcacaacaggctgttctgct
taaattcccttatgttgcgtaaatattgtttacagtcattgtgctgaatggtagtaaataaaaatacagtaattacagtatagag
atgttacatgttataaatattgttacagtcattgtgctgaatggtagtaaataaaatacagtaattacagtatagag
tatacaaactgtgcacaatcaaaggtcagtccatattgttttatttaagtcccccatatatattttaaatcctatttattt
aaaaaacattccagtttcagctgttaaaatgttgtgtggtttgttcaaatgcggttttgattgttgtaaaaatgtcagtttg
atctgttggcaagagcgaattcgcgggcgaaaacgaattgacttttacccatccagaattcgagccctccagacccctcctacacttaac
tcgaaattcctgacttgactttttaaccatccatgaaactgactgagccttgtgccgcaagtcgaggaacttgagagc
cccataacattcagctcccccaccgtctctgcatgtcacagaagtctgtgtgtgtgcgaaccatttggtgtgtgcgaaggaacttgagagc
gtgcgctcttacaaatcccctgtgtgtgtcaggctaattctcaagattctgtcccttccgaaacgcaaataaggtcgagttgtccgttcggtc
atgcggccgcttttgtgtgtgcaggctaattctcaagattctgtcccttccgaaacgcaaataaggtcgagttgtccgttcggtc
tcatgaaattcaggaactgtgccaggcagctgctggcgtcggtagagacgcgagggtgtgttctgtctgcgttcaatgg
gtccctcgagaactgtgccaggcagctgctggcgtcggtagagacgcgagggtgtgttctgtctgcgttcaatgg
aaacggttctcttattcaatggtcttcgtttgg
                                                                              2181
```

Figure 2b

```
+1
tgt tca cct aca ggg ctc agt tat gct aaa att aga ctt gaa aat gca tat    54
Cys Ser Pro Thr Gly Leu Ser Tyr Ala Lys Ile Arg Leu Glu Asn Glu Ala Tyr
                                10 gac gaa gac gga agc tca tta cca gac ttg gct ttt gac agt gat cag att gct   108
Asp Glu Asp Gly Ser Ser Leu Pro Asp Leu Ala Phe Asp Ser Asp Gln Ile Ala
        20                              30 ata cga aac cca cca tct gta att gac gat gtg tat aca tta tat tac cca cca   162
Ile Arg Asn Pro Pro Ser Val Ile Asp Asp Val Tyr Thr Leu Tyr Tyr Pro Pro
            40                                      50
                                                        ─────GHRH-like peptide─────
gag aag aga aca gaa agg cat gct gat gga ata ttt aat gcc tat agg aag      216
Glu Lys Arg Thr Glu Arg His Ala Asp Gly Ile Phe Asn Ala Tyr Arg Lys
                    60                                      70
                                         ↓
gta ctc ggt cag ttg tca gca aga aaa tat cta cat tct gtg atg gca aag cgc  270
Val Leu Gly Gln Leu Ser Ala Arg Lys Tyr Leu His Ser Val Met Ala Lys Arg
                        80                                      90 gta gga ggt gtg agc agt atg gag gaa gat tca gaa cct tta tcc aaa agg cac  324
Val Gly Gly Val Ser Ser Met Glu Glu Asp Ser Glu Pro Leu Ser Lys Arg His
                            100
─────PACAP────────▶+338
tcg gat cgg atc ttc
Ser Asp Arg Ile Phe
110
```

Figure 3.

```
                              ←———————————————— signal peptide ————————————————→
              Met Ser Ser Lys Ala Thr Leu Ala Leu Leu Ile Tyr Gly Ile Ile Met His Tyr Ser Val Tyr
SALMON
HUMAN    Met Thr         Cys         Gly                 Arg                 Val                 Ser
OVINE    Met Thr         Cys         Gly                 Arg             Leu Val                 Ser
RAT      Met Thr         Cys         Gly                 Arg                 Val                 Asn Ser ↓
Ser Ser Pro Leu Gly Leu Asn Tyr Pro Asn Leu Arg Leu Glu Asn Glu Val --- --- Tyr Asp Glu Asp Gly Asn
        Ala Ala Ala Gly Leu Arg Phe Pro Gly Ile Arg Pro Glu Glu Glu Ala             Gly
Gly     Ala Ala Ser Gly Leu Arg Phe Pro Gly Ile Arg Pro Glu Asn Glu Ala
Cys     Ala Ala --- Gly Leu Ser Phe Pro Gly Ile Arg Pro Glu Glu Glu Ala                     Gln Ser Leu Pro Ala Leu Ala Phe Asp Ser Asp Gln Ile Ala Ile Arg Ser Pro Pro Ser Val Ala Asp Asp Leu Tyr
Pro     Asp Phe Gly --- Gly     Glu Pro Pro Gly Ala Gly             Ala     Ala Pro Arg Ala Ala Ala
Pro Gln Gln Asp Tyr ---         Glu Pro Pro Gly Val Gly             Ala     Ala Ala Leu Arg     Ala
Pro     Gln Asp Phe Tyr --- Trp     Pro Pro Pro Gly Ala Gly         Ala     Ala Ala Leu Arg     Ala Thr Leu Tyr Tyr Pro Pro Glu Lys Gly Thr Glu Arg His --- Ala Asp Gly Met Phe Asn Lys Ala Tyr Arg Lys
Ala Trp     Arg         Ala Gly --- --- --- Arg     Asp Val     His     Ile Leu     Glu
Ala         Ala         Ala     --- --- ---         Asp Val     His     Ile Leu Asp
Ala         Ala Asp     Ala     --- --- --- Arg     Asp Val     His Glu Ile Leu     Glu
```

Figure 6a

GROWTH HORMONE-RELEASING HORMONES

| | 1 | 45 | | |
|---|---|---|---|---|
| SALMON   | HADGMFNKAYRKALGQLSARKYLHSLMAKRVGGGSTMEDDTEPLS | (OH) | 100% |
| CARP     | ..................T.....MI...N.... | (OH) | 91% |
| CATFISH  | ...LLDR.L.DI.V........T.V...EEEED.E.S.... | (OH) | 62% |
| STURGEON | ....I......V.............V....V.S..E.S.... | (OH) | 84% |
| MOUSE    | .V.AI.TTN...L.S..Y...VIQDI.N.Q--ERIQEQ--RAR.. | (OH) | 38% |
| RAT      | ...AI.TSS..RI....Y...L..EI.NRQQ.ERNQEQ--RSRFN | (OH) | 38% |
| SHEEP    | Y..AI.TNS...I........L.QDI.NRQQ.ERNQEQGAKVR. | (NH2) | 40% |
| GOAT     | Y..AI.TNS...V........L.QDI.NRQQ.ERNQEQGAKVR. | (NH2) | 40% |
| COW      | Y..AI.TNS...V........L.QDI.NRQQ.ERNQEQGAKVR. | (NH2) | 40% |
| PIG      | Y..AI.TNS...V........L.QDI.SRQQ.ERNQEQGARVR. | (NH2) | 40% |
| HUMAN    | Y..AI.TNS...V........L.QDI.SRQQ.ESNQERGARAR. | (NH2) | 40% |

FIGURE 7

```
CLONE SS/RACE 7
CGTTTTCCTCAGTCTCCTGACTCTGTGGAAATGTTAGATAGCCCTTCGCACATTTAACGTTGTGATATTTTCTTCCCCACAGCAGAACA
                                                                     -9
CLONE SS/RACE 2                GACATCCAGCTTGTCTCTCCACACGGTAATAGCAGGACA

CLONE CS/LIBa   CACGAGCCGGATCCGATACAGGCGTCTATTTCGACACTGGAATAGCAGGACA

CLONE CS/LIBb         GCACGAAGACAGGCTTGGGTACTTTAGAATGTTTGGAGCAGGACA
```

Figure 8

```
                A
SALMON  CGTTGCTAACCCAAACTACCATGTGTACAGCCCAGAT---------CAAGTCATTTTGAGATA---
        ** * **        *** ** ***** *********                ***** **** * *
HUMAN   CGATGGGTTACCAGCTACCC-TGTGTATACAGCCCTGACGCAATGAAAAGTCGTTTT-CCAAACTG
OVINE   CGACGAGTTACCAGCTATCC-TGTGTATACAGCCCTGACACAATGAGAAGTCGTTTTCCCAACTG
RAT     CGATGAGTTGCCAGCTACCG TGTGTAT---------AAAATGAAAAGTCGTTTT-CCAAATTG

----G
ACTGAACAATCAATCAGTGG-ATCGCTCTTGTGTTCTTT--AAACATGTATTTATGTA-TGAAGTAAA
********** ***       ******* ************                  ***********
ACTCAACAGT---------CATCGCTCGTGTGTTCTATCCAAACATGTATTTATGTAATGAAGTAAA
ACTGAACTGT---------CATCGCTGCTGTGTTCTGTCCC-ACATGTATTTATGTA-TGAAGTCAA
ACTGACCAGTCAT------CACTCA---TGTGTTCTTCCAAACATGTATTTATGTA-TCAAGTAAA

T      C
GCCATTAAAATGAATATTTGATAAT
********* ***************
GCCATTAAA-TGAATATTTGATAAT
GCCATTAAA-TGAATATTTGATAAT
GCCATTAAA-TGACTATTTGATAAT
```

Figure 9

```
                                          -51
CS/LIBa         A              CACGAGCCGGATCCGATACAGCGTCTAT
CS/LIBb         B               GCACGAGACAGGCTTGGGTAC
                                    +1
TTCGACACTGGAATAGCAGGACA ATG TCT AGT AAA GCG ACT TTA GCC TTA        27
TTTAGAATGTTTGGAGCAGGACA ATG TCT AGT AAA GCG ACT TTA GCC TTA
                        Met Ser Ser Lys Ala Thr Leu Ala Leu 10                              20           ***
CTC ATC TCT GGA ATC ATA ATG CAC TAC AGT GTC TAC TGC TCA CCT        72
CTC ATC TCT GGA ATC ATA ATG CAC TAC AGT GTC TAC TGC TCA CCT
Leu Ile Tyr Gly Ile Ile Met His Tyr Ser Ile Tyr Cys Ser Pro

30
CTC GGG CTT AAC TAT CCT AAC CTT AGA CTT GAA AAT GAG GTT TAT        117
CTC GGG CTT AAC TAT CCT AAC CTT AGA CTT GAA AAT GAG GTT TAT
Leu Gly Leu Asn Tyr Pro Asn Leu Arg Leu Glu Asn Glu Val Tyr 40                                      50
GAC GAG GAT GGG AAT TCG TTA CCG GCC TTG GCT TTT GAC AGC GAT        162
GAC GAG GAT GGG AAT TCG TTA CCG GCC TTG GCT TTT GAC AGC GAT
Asp Glu Asp Gly Asn Ser Leu Pro Ala Phe Gly Phe Asp Ser Asp

60
CAA ATT GCT ATA AGA AGT CCC CCG TCT GTG GCT GAC GAT TTG TAC        207
CAA ATT GCT ATA AGA AGT CCC CCG TCT GTG GCT GAC GAT TTG TAC
Gln Ile Ala Ile Arg Ser Pro Pro Ser Val Ala Asp Asp Leu Tyr

70                              V       80
ACT TTA TAC TAC CCA CCG GAG AAA AGT GGA GGG AGC ACC ATG GAA        252
ACT TTA TAC TAC CCA CCG GAG AAA AGT GGA GGG AGC ACC ATG GAA
Thr Leu Tyr Tyr Pro Pro Glu Lys Ser Gly Gly Ser Thr Met Glu
                                    Λ
GAC GAC ACA                         deletion of exon 4 which
GAC GAC ACA                         contains GHRH 1-32
Asp Asp Thr
```

SALMON GHRH VS GLUCAGON SUPERFAMILY

```
GHRH salmon    HADGMFNKAYRKALGQLSARKYLHSLMAKRVGGGSTMEDDTEPLS (OH)
PHM-27         ....V.TSDFS.L......K...E...       (NH2)       67%
PHI-27 rat     ....V.TSD.SRL...I.K...E..I        (NH2)       59%
VIP dogfish    .S.AV.TDN.SRIRK.MAVK..IN..L.      (NH2)       36%
VIP human      .S.AV.TDN.TRLRK.MAVK...N.ILN      (NH2)       32%
GLUCAGON salmon .SE.T.SND.S.YQEERM.QDFVQW..NS                28%
GLP salmon     ....TYTSNVSTY.QDQA.KDFVSW.KSG.A               26%
SECRETIN human .S...T.TSELSRLREGARLQRL.QG.V      (NH2)       22%
GIP human      Y.E.T.ISD.SI.MDKIHQQDFVNW.L.QKGKKNDWKHNI.Q. (OH) 19%
```

SALMON PACAP VS GLUCAGON SUPERFAMILY

| | | |
|---|---|---|
| PACAP salmon | HSDGIFTDSYSRYRKQMAVKKYLAAVLGKRYRQRYRNK (NH$_2$) | |
| VIP dogfish | ...AV...N...I..........INSL.A (NH$_2$) | 68% |
| VIP human | ...AV...N.T.L..........NSI.N (NH$_2$) | 68% |
| PHM-27 | .A..V..SDF.KLLG.LSA....ESLM (NH$_2$) | 41% |
| SECRETIN human | ....T..SEL..L.EGARLQRL.QGLV (NH$_2$) | 37% |
| GHRH salmon | .A...M.NKA.RKALG.LSAR...HSLMA..VGGGSTMEDDTEPLS (OH) | 29% |
| | 9/27 | 33% |
| GLP salmon | .A..TY.SNV.T.LQDQ.A.DFVSWLKSG.A | 29% |
| | 8/27 | 30% |
| GLUCAGON salmon | ..E.T.SND..K.QEERMAQDFVQWLMNS | 24% |
| GIP HUMAN | YAE.T.ISD..IAMDKIHQQDFVNWL.AQKGKKNDWKHNITQ (OH) | 12% |
| | 5/27 | 19% |

Figure 13b

```
sGHRH   H-ADGMFNKAYRKALGQLSARKYLHSLMAKRVG----GGSTMEDDTEPLS

OVINE   DV.H.ILD.....V.D......R..QT....GL.GTPG..A---D..S....   28/48=58%

HUMAN   DV.H.IL.E....V.D......G.H.Q..V.RG..GSLG..A---G..A....   27/48=56%

RAT     DV.HEIL.E....V.D.........Q.MV.RGM.ENLAAAA--V..RA..T    22/48=46%
```

FIGURE 14

```
catfish Met ala lys ser ser arg ala thr leu ala leu leu ile tyr gly ile leu met arg tyr
        atg gcc aaa tct agt aga gct act ttg gct ctg ctc atc tac ggg atc tta atg cgc tac
        atg tct agt aaa gcg act tta gcc tta ctc atc tat gga atc atg cac tac
salmon  Met ser ser lys ala thr leu ala leu leu ile tyr gly ile ile met his tyr ser gln cys thr --- pro ile gly met gly phe pro asn met arg leu asp asn asp val
agc caa tgc aca --- ccc atc gga atg ggc ttc ccc aat atg agg cta gac aac gac gtg
agt gtc tac agc tca cct ctc ggg ctt aac tat cct aac ctt aga ctt gaa aat gag gtt
ser val tyr ser ser pro leu gly leu asn tyr pro asn leu arg leu glu asn glu val phe gly asp glu gly asn ser leu ser glu leu ser tyr glu pro asp thr met ser ala
ttc ggg gac gag gga gat ggg aat tcg tta agt gag ctg tcc tac gag ccg gac acg atg agc gcg
tat gac gag gag gat ggg aat tcg tta ccg gcc ttg gct ttt gac agc gat caa att gct ata
tyr asp glu glu asp gly asn ser leu pro ala leu ala phe asp ser asp gln ile ala ile arg ser arg pro ala leu pro glu asp ala tyr thr leu tyr tyr pro glu arg arg
cgc agt cgt cca gcc ctc cct gaa gac gca gat tta tac act cta tac cca ccg gag aga aga
aga agt ccc ccg tct gtg gct gac gat tta tac act tta tac tac cca ccg gag aaa gga
arg ser pro ser val ala asp asp leu tyr thr leu tyr tyr pro pro glu lys gly ala glu thr his ala asp gly leu leu asp arg ala leu arg asp ile leu val gln leu
gcc gaa acg cat gca gac gga ttg tta gat aga gcc ttg agg gac atc ctg gtt cag tta
acg gaa agg cat gca gac gga atg tct aat aaa gcc tac agg aaa gcg ctg ggt cag tta
thr glu arg his ala asp gly met phe asn lys ala tyr arg lys ala leu gly gln leu
```

Figure 15a

```
ser ala arg lys tyr leu his ser leu thr ala val arg val gly glu glu glu glu asp
tca gcc cga aaa tat ctg cat tct ctg acg gca gtt cgc gta ggt gag gaa gag gag gat
tca gca aga aaa tat ctt cat tct ctg atg gca aag cgt gta ggt gga ggg agc acc atg
ser ala arg lys tyr leu his ser leu met ala lys arg val gly gly gly ser thr met glu glu asp ser glu pro leu ser lys arg his ser asp gly ile phe thr asp ser tyr
gaa gag gac tcg gag cca tcg aag cgc cac tcg gac ggc att ttc acg gac agc tac
gaa tac tac aca gag cct ctg tca aag cga cat tcg gat ggg atc ttc aca gat agc tac
glu asp asp thr glu pro leu ser lys arg his ser asp gly ile phe thr asp ser tyr ser arg tyr arg lys gln met ala val lys ile pro cys ser ser ala gly lys lys
tcg cgc tac cgg aaa caa atg gcc gta aaa ata cct tgc agc agt gct ggg aag aag
agc cgc tac cga aag caa atg gca gtc aag tac ctg gcg gca gtc ctt ggg aaa agg
ser arg tyr arg lys gln met ala val lys tyr leu ala ala val leu gly lys arg val gln thr glu arg ala ala asn ser arg arg ile gly cys thr ile ser leu asp gly
gta cag aca gag cgg gcc gcg aat tcg cgc cgc att ggt tgt acc atc agt ttg gac ggg
tat aga cag aga tat aga acc aaa gga cgc cgc cta ggc tat ctg tag
tyr arg gln arg tyr arg asn lys gly arg arg leu gly tyr leu *** his AMB
cat tag
```

Figure 15b

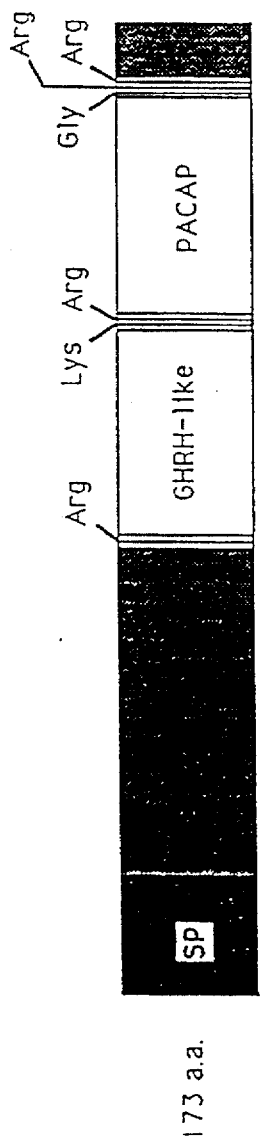
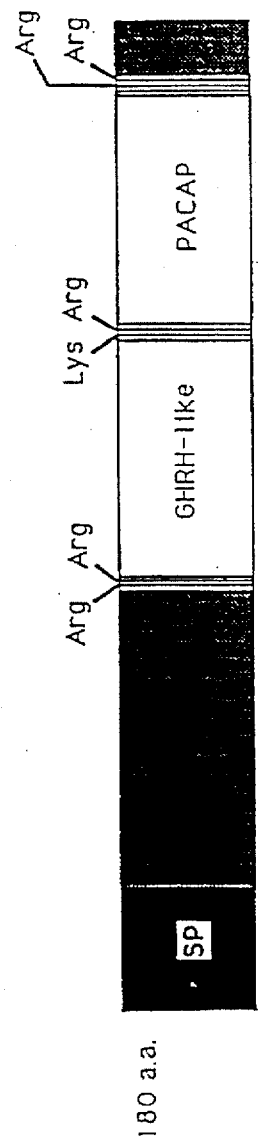
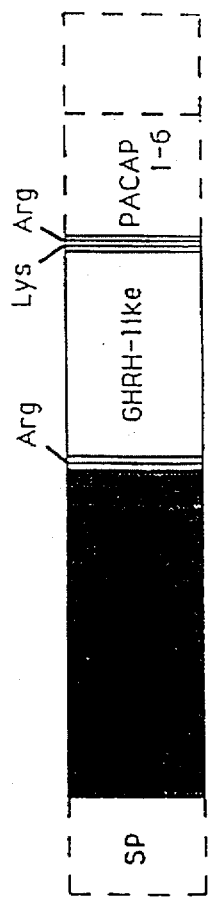
FIGURE 16

DNA ENCODING TWO FISH NEUROPEPTIDES

The present invention relates to fish neuropeptides. More particularly, it relates to novel cDNA sequences coding for precursors of two fish neuropeptides, pituitary adenylate cyclase activating polypeptide (PACAP) and growth hormone-releasing hormone-like peptide (GHRH-like peptide), and to novel precursor proteins for these two peptides. It relates also to methods for producing enhanced growth of fish.

BACKGROUND OF THE INVENTION

The glucagon superfamily contains a number of members including glucagon, vasoactive intestinal polypeptide (VIP), peptide histidine methionine (PHM), peptide histidine isoleucine (PHI), secretin, gastric inhibitory peptide, growth hormone-releasing hormone (GHRH), helospectin and helodermin. Recently, two new candidates, pituitary adenylate cyclase activating peptide (PACAP) and PACAP-related peptide (PRP) were added for mammals. Structurally, they resemble VIP and GHRH, respectively.

cDNAs coding for PACAP have been obtained from sheep, rats and humans [Ogi et al., (9), Kimura et al., (8)]. In mammals, these cDNAs also code for a second peptide called PACAP-related peptide or PRP [Ogi et al., (9), Kimura et al., (8)]. No biological function has so far been reported for PRP and it has not yet been isolated from mammalian tissues.

Another member of the glucagon superfamily, GHRH, is encoded in mammals in a separate gene in a separate chromosome from the gene for PACAP and PRP (Mayo et al., 66).

Mammalian GHRH stimulates the synthesis of growth hormone (GH) in the anterior pituitary, stimulates release of GH from anterior pituitary cells both in vivo and in vitro, stimulates an increase in proliferation of GH-producing cells, stimulates an increase in GH mRNA in pituitary cells in vitro and induces transcription of the GH gene in cell culture and in vivo. Mammalian GHRH does not stimulate release of other pituitary hormones (62, 38, 33, 64, 65, 67, 68 and 63).

Much less is known about PACAP and GHRH in fish. Vaughan et al., (11), have isolated a GH-releasing factor from carp hypothalamic tissue and determined its amino acid sequence. Fish PACAP has not been reported prior to the work of the present inventors.

It was therefore not previously known whether fish PACAP, if it existed, is encoded on a gene which also encodes an additional peptide, as for mammalian PACAP.

The present inventors have now shown that there is a PACAP in fish and that this peptide is encoded along with an additional peptide on one gene.

Surprisingly, they have shown that in fish, this second peptide is a GHRH-like peptide. This second peptide appears to be equivalent to mammalian GHRH which is encoded on a quite separate chromosome from PACAP in mammals.

SUMMARY OF INVENTION

In accordance with one aspect of the invention, novel DNA molecules are provided comprising nucleotide sequences encoding fish GHRH-like peptide and fish PACAP or encoding both peptides.

In accordance with a further aspect of the invention, fish PACAP and GHRH-like peptide precursor proteins are provided.

In accordance with a further aspect of the invention, substantially pure fish PACAP and substantially pure fish GHRH-like peptide are provided.

In accordance with a further aspect of the invention, a method is provided for producing fish PACAP and fish GHRH-like peptide, as well as novel hosts transformed with DNA molecules encoding these peptides.

In accordance with a further aspect of the invention, novel DNA constructs are provided comprising the novel DNA molecules of the invention operatively associated with a suitable promoter and transcription termination sequence.

In accordance with a further aspect of the invention, a method is provided for producing enhanced growth of a fish comprising introducing into fertilised eggs of the fish novel DNA constructs of the invention whereby expression of the DNA construct during growth of the eggs into fish produces PACAP and GHRH-like peptide and gives enhanced growth of the fish.

In accordance with a further aspect of the invention a method is provided for identifying a transgenic fish containing a DNA construct comprising a transfected DNA flanked by at least one heterologous DNA sequence comprising the steps of obtaining a sample of DNA from said fish; amplifying the DNA of the sample by PCR using at least one primer DNA sequence hybridisable to a portion of the DNA construct in the region of the junction between the transfected DNA and the at least one heterologous DNA sequence; and detecting said amplified DNA which is indicative of a transgenic fish.

DESCRIPTION OF DRAWINGS

Certain embodiments of the invention are described, reference being made to the accompanying drawings wherein:

FIG. 1 shows the nucleotide sequence (Sequence ID NO: 1) and deduced amino acid sequence (Sequence ID NO: 6) of sockeye salmon GHRH/PACAP cDNA. The putative signal peptide and polyadenylation signal (ATTAAA) are underlined. The GHRH-like peptide, amino acids 82–126, and PACAP38, amino acids 129–166, are boxed. Nucleotide substitutions and resulting amino acid changes noted in additional clones are shown below the main reading frame.

FIG. 2 shows the nucleotide sequence (Sequence ID NO: 2) and deduced amino acid sequence (Sequence ID NO: 7) of Thai catfish GHRH/PACAP cDNA.

FIG. 3 shows the nucleotide sequence (Sequence ID NO: 3) and deduced amino acid sequence (Sequence ID NO: 11) of a portion of sturgeon GHRH/PACAP cDNA.

FIG. 4A shows amplification of double stranded cDNA using primer CSC33 (5'CA(T/C)GCIGA(T/C)GGIATGTT (T/C)AA3' (Sequence ID NO: 12)) and primer oligo (dT) (GAATTCT(dT)36) [UT=untranslated];

FIG. 4B shows reverse transcription using sequence specific primer NMS3 (5'TCGGTAGCGGCTGTAGCTATCTG3' (Sequence ID NO: 15)) to obtain 5' region;

FIG. 4C shows tailing of single stranded cDNA with dATP and subsequent amplification using internal primer NMS1 (5'TGACAGAGGCTCTGTGTC3' (Sequence ID NO: 14)) and primers #2 (GGCTCGAGCCCGGGAATTCCG(dT) 15 (Sequence ID NO: 18)) and #3 (5'GGCTCGAGGCCCGGGAATTCCG3' (Sequence ID NO: 19)) [SP=signal peptide].

FIG. 7 shows a comparison of the deduced amino acid sequence of salmon GHRH-like peptide (Sequence ID NO: 8) with the deduced amino acid sequences of catfish (Sequence ID NO: 24) and sturgeon (Sequence ID NO: 25) GHRH-like peptides and with the deduced sequence of mouse GHRH (Sequence ID NO: 26) and the reported sequences of carp, rat, sheep, goat, cow, pig and human GHRHs (Sequence ID NOS: 23 and 29 to 32). Amino acids different from the salmon molecule are shown as letters and identical residues are shown by the dots (.). Bars (—) represent spaces where the sequence was shifted to obtain maximum alignment of the peptides. Percent sequence identity to the salmon hormone is shown on the right.

FIG. 8 shows a comparison of all the GHRH/PACAP precursor clones that contained a 5' untranslated region (Clone SS/RACE 7—Sequence D NO: 48; clone SS/RACE 2—Sequence ID NO:49; clone CS/LIBa—nucleotides −51 to −1 of Sequence ID NO: 4; clone CS/LIBb—nucleotides −44 to −1 of Sequence ID NO: 5). Identical nucleotides among the different clones are in bold and underlined (single). Additional start codons (ATG) are double underlined. Nucleotides are numbered negatively from the start codon (not shown) on right.

FIG. 9 shows a comparison of the 3' untranslated region of the salmon preproGHRH/PACAP (Sequence ID NO: 33) with the beginning of the 3' untranslated regions of human, ovine and rat preproPACAPs (Sequence ID NOS: 34 to NO: 33). Nucleotides identical to the salmon for any of the three mammalian forms are shown by an *. Where a nucleotide is not identical to the salmon, but at least one of the mammalian forms is, this nucleotide is in bold. Gaps (—) were inserted for maximum sequence alignment. The salmon polyadenylation (ATTAAA) is underlined. Nucleotide changes in clone SS/PCR 5 are shown above the salmon clone SS/PCR 4 sequence.

FIG. 10 shows the nucleotide sequences from clones CS/LIBa (A) (Sequence ID NO: 4) and CS/LIBb (B) (Sequence ID NO: 5) and deduced amino acid sequence (Sequence ID NO: 10) of chum salmon short precursor cDNA. Nucleotides in the 5' untranslated region which are different in the two clones are shown in bold. A putative ATG start codon in the 5' untranslated region of clone CS/LIBb is shown by the double underline. A Cys in position 22, represented by ***, is identical to the full length clone SS/PCR 7, but different from that of SS/PCR 2. Putative signal peptide is underlined.

FIGS. 13A and B shows salmon GHRH-like peptide (Sequence ID NO: 8) (A) and salmon PACAP-38 (Sequence ID NO: 9) (B) compared to the other members of the glucagon superfamily (PHM-27—Sequence ID NO: 37; PHI-27—Sequence ID NO: 38; VIP dogfish—Sequence ID NO: 39; VIP human—Sequence ID NO: 40; glucagon salmon—Sequence ID NO: 41; GLP salmon—Sequence ID NO: 42; secretin human—Sequence ID NO: 43; GIP human—Sequence ID NO: 44). Amino acids identical to the salmon sequences are shown by the dots (.). Percent sequence identity to the salmon sequences is shown on the right. GHRH=growth hormone releasing hormone; PHM-27=peptide histidine-methionine; PHI-27=peptide histidine-isoleucine; VIP—vasoactive intestinal peptide; GLP=glucagon-like peptide; GIP=gastric inhibitory peptide; PACAP=pituitary adenylate cyclase activating polypeptide.

FIG. 14 shows a comparison of salmon GHRH-like peptide (Sequence ID NO: 8) with mammalian PRP's (48 amino acids ovine—Sequence ID NO: 45, human—sequence ID NO: 46; rat—Sequence ID NO: 47).

FIG. 15 shows a comparison of catfish and salmon cDNA and derived amino acid sequences.

FIG. 16 shows a schematic diagram comparing the precursor for salmon, catfish and sturgeon GHRH/PACAP, deduced from cDNA sequences (a.a=amino acids).

DETAILED DESCRIPTION OF THE INVENTION

In the description which follows, references are made to certain literature citations which are listed at the end of the specification.

The following abbreviations are used in the specification:

| | |
|---|---|
| CS | chum salmon |
| LIB. | library |
| PCR | polymerase chain reaction |
| RACE | rapid amplification of cDNA ends |
| SS | sockeye salmon |

The inventors have isolated and characterised novel fish cDNA sequences which code for unique precursor proteins which contain two biologically active hormones. The hormones encoded in these novel cDNA sequences are a GHRH-like peptide and PACAP.

Similar organization of the fish cDNA has been found in all three species examined, salmon, catfish and sturgeon.

This is in complete contrast to the mammalian genome, where PACAP is encoded on a gene also coding for PRP, while the GHRH gene occurs on a separate chromosome.

Isolation and Identification of Salmon GHRH/PACAP DNA and Precursor Sequences using PCR and RACE A novel cDNA was isolated from sockeye salmon brain by using PCR with a combination of novel primers.

mRNA was isolated from brain tissue and cDNA was prepared as described in Example 1.1.

Figure 4:
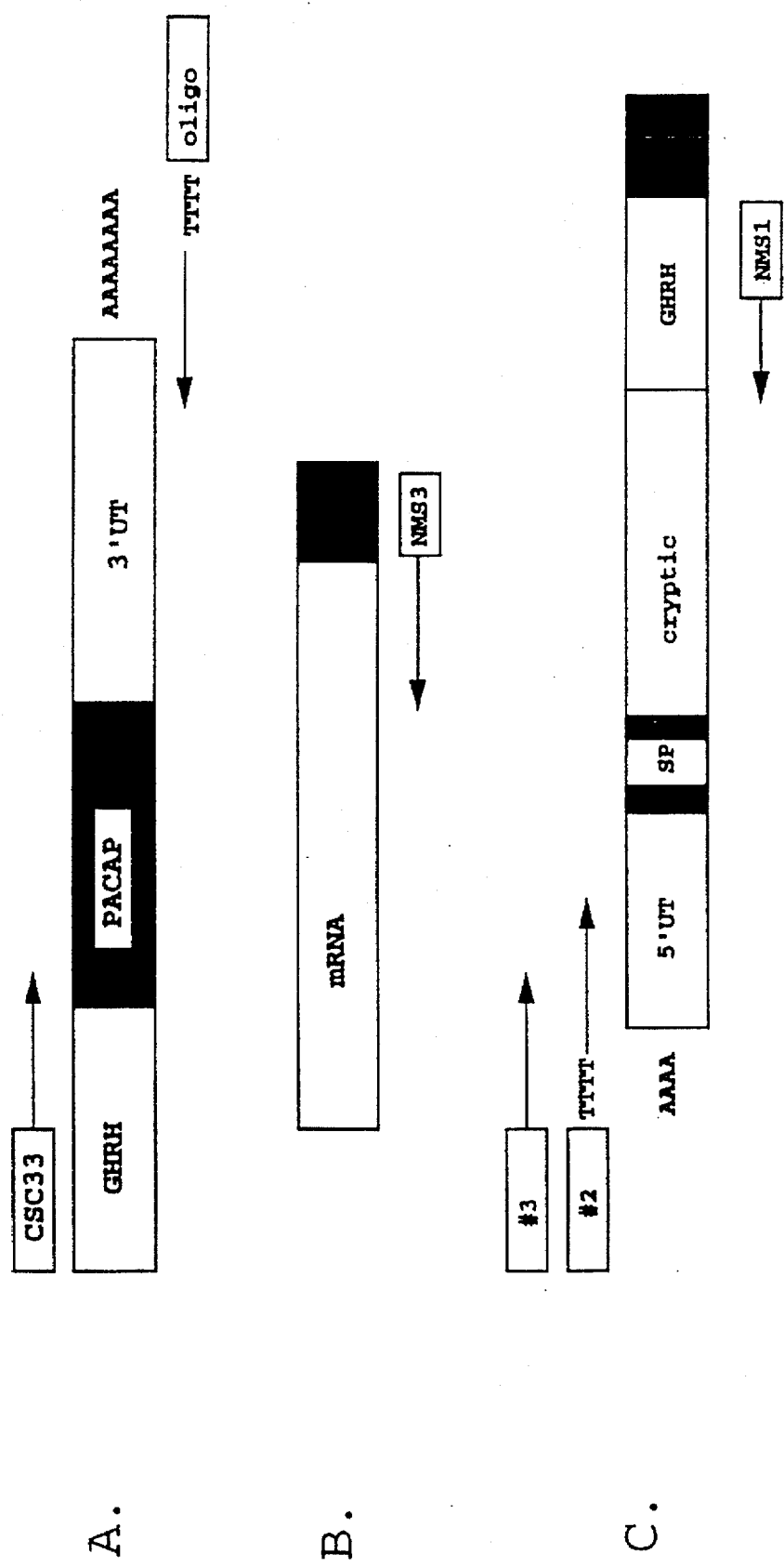
FIGS. 4A–C is a schematic diagram of the strategy used for PCR and RACE to amplify salmon cDNA.

The cDNA was amplified as described in Example 1.2 and 1.3, the strategy being set out in FIG. 4. The DNA was cloned and sequenced as described in Example 1.4 and 1.5.

A degenerate primer CSC33 based on conserved sequences of GHRH peptides in human, rat and carp was used with an oligo dT primer in the PCR to amplify a 425 bp cDNA fragment (FIG. 4A). This cDNA was subsequently cloned into pBluescript KS II. Two clones designated SS/PCR 4 and SS/PCR 5 were sequenced and each was found to contain a GHRH-like and PACAP sequence (bp position 244–668, FIG. 1).

Figure 1:
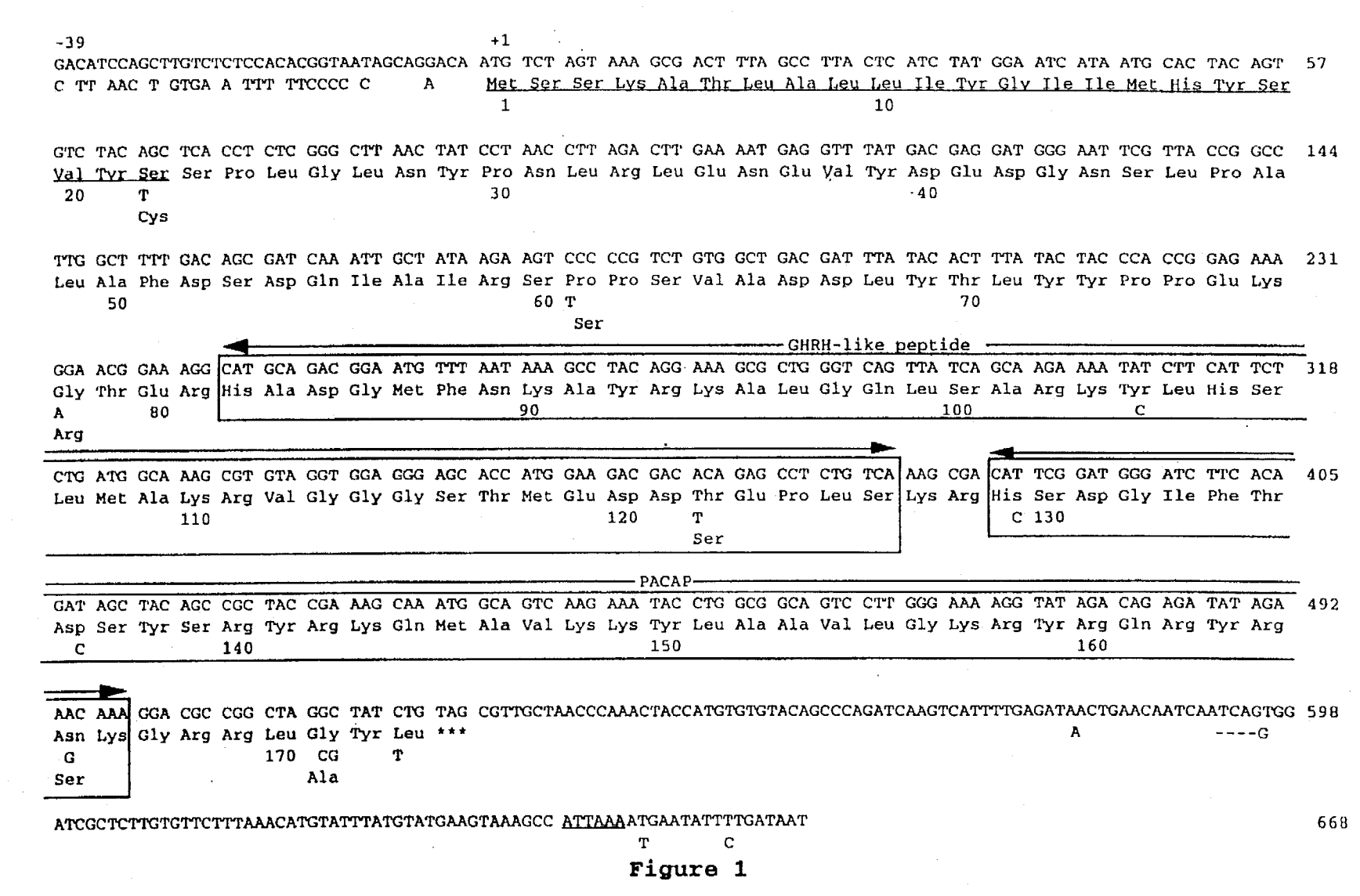

These two clones differed at 12 bp positions and clone SS/PCR 5 had a deletion of 4 bases (FIG. 1). Three amino acid substitutions between the clones resulted from the nucleotide changes (FIG. 1).

To identify the cDNA sequence 5' to the coding region of the GHRH-like region, the RACE reaction was used (FIG. 4B and 4C). A cDNA fragment of approximately 417–462 bp was cloned and sequenced (bp positions −84 to 378 (FIG. 1). Two of 32 plasmid preparations contained the 5' GHRH-like region as identified with PCR. These two clones, SS/RACE 2 and SS/RACE 7, were different at 3 nucleotide positions within the translated region resulting in 3 amino acid changes (FIG. 1). The 5' untranslated regions are discussed below.

Figure 5:
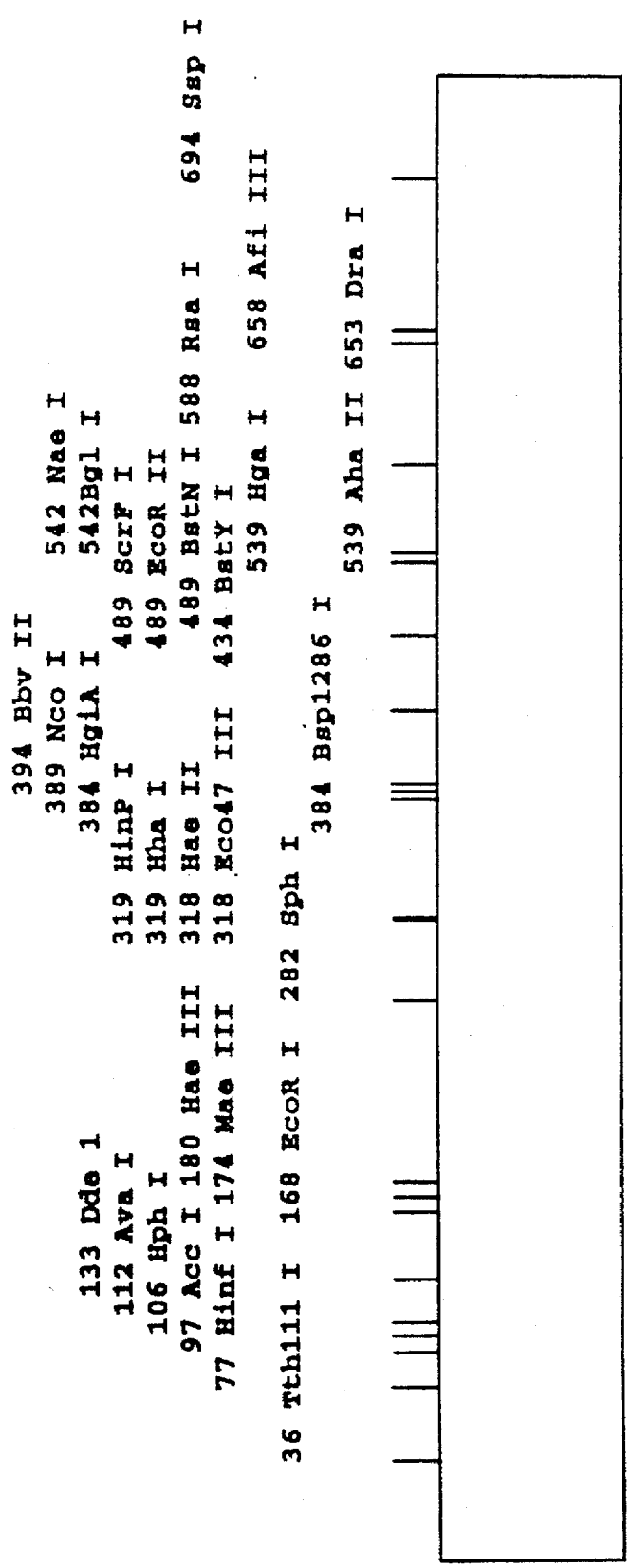
FIG. 5 shows a restriction map of sockeye salmon GHRH/PACAP cDNA indicating the unique restriction sites.

A full length GHRH/PACAP cDNA was obtained by digesting the two overlapping clones, SS/RACE 2 and SS/PCR 4, with Nco I (FIG. 5) and Not I. The cleavage site for the restriction enzyme Not I is located in the multiple cloning region of pBluescript II KS. After removal of the fragment from clone SS/PCR 4, the fragment obtained from clone SS/RACE 2 was ligated into clone SS/PCR 4. This resulted in a PACAP cDNA clone of 707 bp with an open reading frame of 173 amino acids.

This cDNA was sequenced as described in Example 1.5 and the nucleotide sequence is shown in FIG. 1.

Organization of the Salmon GHRH/PACAP Precursor

The deduced amino acid sequence corresponding to salmon GHRH/PACAP cDNA is also shown in FIG. 1.

The salmon GHRH/PACAP precursor protein has 173 amino acids comprising four distinct domains: a signal peptide (22 residues), a cryptic peptide which follows the signal peptide (59 residues), the GHRH-like region (45 residues) and PACAP (38 residues).

Figure 6B:
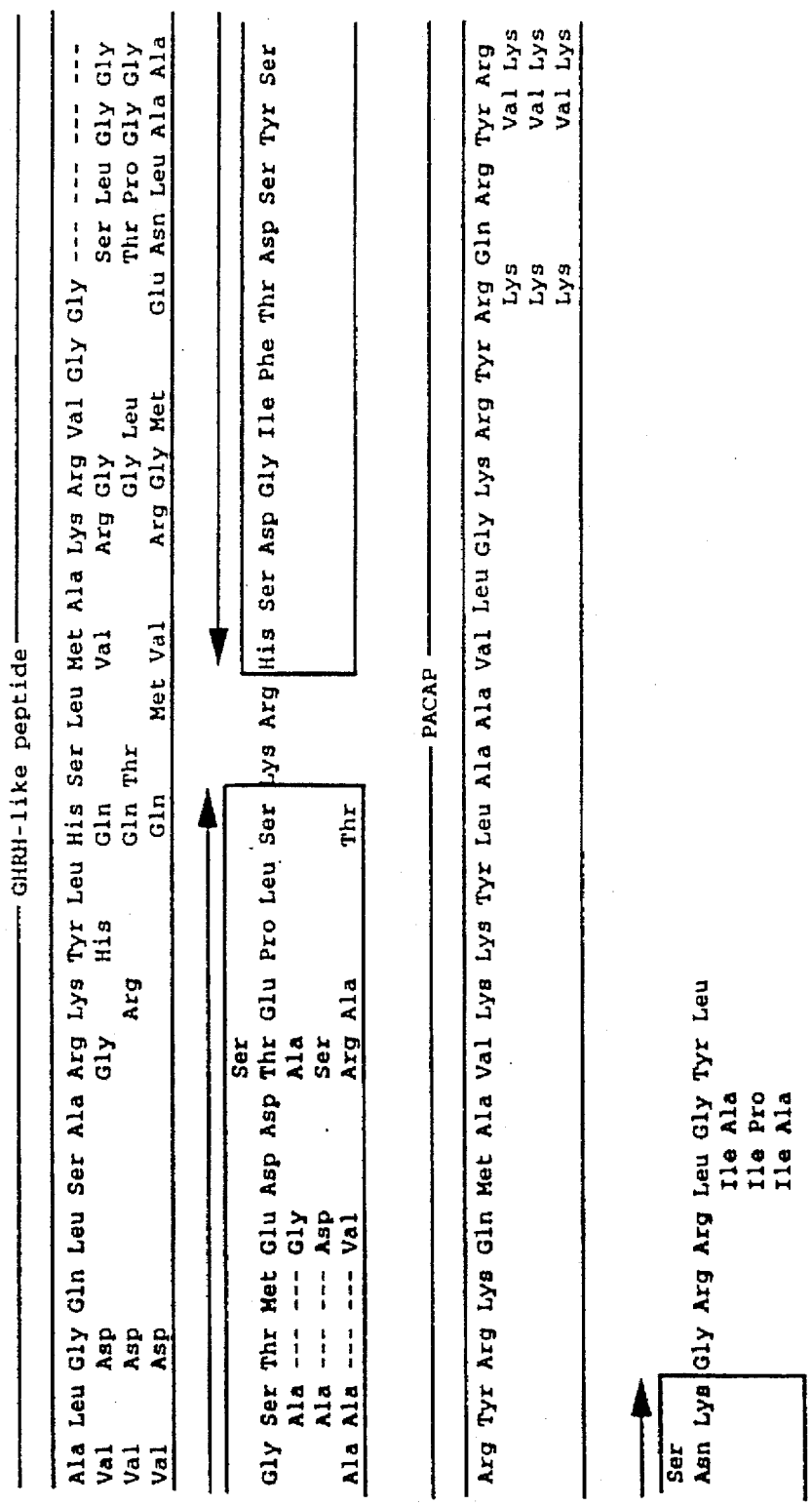
FIG. 6 shows a comparison of salmon GHRH/PACAP precursor (Sequence ID NO: 6) with the three mammalian PACAP precursors, human (Sequence ID NO: 20), ovine (Sequence ID NO: 21) and rat (Sequence ID NO: 22). Amino acids different from the salmon precursor are shown, while identical residues are not. The signal peptide of the salmon precursor is underlined and the peptide regions of all the precursors are boxed.

The signal peptide of the salmon GHRH/PACAP precursor has a hydrophobic core and is two amino acids shorter than the signal peptide of the ovine [8], human [1,8] and rat [9] PACAP precursors (FIG. 6). At the amino acid level, there is 77% sequence identity between the salmon signal peptide and human PACAP signal peptide. A cysteine at position 22 of the signal peptide in some of the salmon GHRH/PACAP clones is identical to that of the rat, while the serine in clone SS/PCR 4 is the same as the human cDNA (FIG. 4).

The presence of two dibasic enzyme processing sites and a single arginine enzyme processing site would be expected to result in the cleavage of the precursor into a GHRH-like peptide of 45 amino acids with a free hydroxyl carboxy terminus and a PACAP of 38 amino acids with an amidated carboxy terminus. The single Arg processing site precedes the GHRH-like molecule and the dibasic Lys-Arg processing site follows (FIGS. 1 and 6).

The salmon PACAP is preceded by a Lys-Arg enzyme processing site and has a Gly-Arg-Arg at its carboxy terminus. In addition, within the GHRH-like peptide, there is a Lys-Arg site; cleavage at this site will result in a 28 residue peptide, GHRH-like peptide 28.

Within the PACAP-38 peptide, there is a Gly-Lys-Arg site; processing at this site will give a 27 residue peptide, PACAP-27.

Isolation and Identification of Catfish GHRH/PACAP DNA and Precursor Sequences using a Catfish Probe to Screen a cDNA Catfish Brain Library A novel cDNA was isolated from catfish by screening a catfish brain cDNA library with a catfish GHRH/PACAP probe synthesized by PCR.

mRNA was isolated from brain tissue and cDNA was prepared as described in Example 4.1.

A cDNA library was prepared from catfish brains; a lysate was then prepared from the library as described in Example 4.2.

Nondegenerate primers [SP1, NMS3, NMS4] based on the salmon GHRH/PACAP cDNA sequence were used with the catfish lysate DNA in a polymerase chain reaction (PCR) to amplify a 393 bp cDNA fragment as described in Example 4.3. This cDNA was subsequently cloned into pBluescript KS II as described in Example 4.4. The cloned cDNA was sequenced as described in Example 4.5 and found to contain a sequence that included the coding for a complete GHRH-like peptide and a partial PACAP sequence (bp positions 43 to 429, FIG. 2).

To isolate a full length cDNA clone, the 393 bp PCR fragment was used as a probe to screen the catfish cDNA library as described in Example 4.6. One positive clone was isolated and sequenced as described in Example 4.7. The sequence of this full length clone of approximately 2500 bp is shown in FIG. 2. A Northern blot was done with the 393 bp probe as described in Example 4.8 to confirm that one band on the blot was similar in size with the cDNA shown in FIG. 1.

| | |
|---|---|
| SP1: 5'GGAATCATAATGCACTACAG TGTC 3' | (Sequence ID NO: 15) |
| NMS 4: 5'CTACACGCTTTGCCATC AGAGA 3' | (Sequence ID NO: 16) |

Isolation and Identification of Sturgeon GHRH DNA and Precursor Sequences using PCR A novel cDNA was isolated from sturgeon brain by using PCR with a combination of primers made to the salmon cDNA.

mRNA was isolated from brain tissue and cDNA was prepared as described in Example 5.1.

The cDNA was amplified, cloned and sequenced as described in Example 5.2.

Nondegenerate primers [SP1 and NMS3] based on the salmon GHRH/PACAP sequence were used with sturgeon single stranded cDNA in a polymerase chain reaction to amplify a 339 bp cDNA fragment as described in Example 5.2. This cDNA was subsequently cloned into pBluescript KS II and sequenced as described in Example 5.2. The cDNA fragment was found to contain a sequence that included the coding for a complete GHRH-like peptide and a partial PACAP sequence (bp positions 1 to 339, FIG. 3).

The nucleotide sequences of catfish and sturgeon cDNA are shown in FIGS. 2 and 3 respectively, as well as the corresponding amino acid sequences.

The catfish GHRH/PACAP precursor protein has 180 amino acids and comprises the same four domains as the salmon protein.

The catfish and salmon precursors contain signal and cryptic peptides that are similar in length, but have only 68% (signal peptide) or 48% (cryptic peptide) sequence identity. The catfish and salmon GHRH-like peptides are both 45 amino acids, although the catfish GHRH may have an extended amino terminus of 3 amino acids, depending on the cleavage site. If the arg-arg site (amino acid positions 78–79, FIG. 2) is cleaved, catfish GHRH would be expected to be 48 amino acids, but if the Thr site (amino acid position 82) is cleaved, catfish GHRH would be expected to be 45 amino acids. The catfish and salmon GHRH have 62% sequence identity. Both catfish and salmon precursors have a dibasic enzyme processing site between GHRH and PACAP. The catfish and salmon PACAP precursors have cleavage sites that would be expected to produce PACAP27 and/or PACAP38 (salmon) or PACAP39 (catfish). Catfish PACAP27 has 78% and PACAP39 has 61% sequence identity to salmon PACAPs. PACAP39 in catfish is not expected to be amidated. Both catfish GHRH45 and PACAP have histidine at the amino terminus.

The PCR product prepared from sturgeon brain cDNA contained a region from the end of the signal peptide to amino acid 6 of PACAP. The complete GHRH sequence derived from this PCR product showed a 45 amino acid peptide with a free hydroxyl carboxy terminus. Sturgeon GHRH-like peptide has higher (84%) sequence identity to salmon GHRH than does catfish GHRH. A dibasic enzyme processing site separates the GHRH-like peptide from the amino terminus of PACAP as described for the salmon and catfish precursors.

The amino acid sequence identity of the various peptides of salmon, catfish and partial sturgeon precursors are shown in Table I in relation to each other and in Table II in relation to human PACAP precursor. FIG. 16 shows the peptide positions in the three precursors.

In accordance with one embodiment of the present invention, novel cDNAs are provided which are useful for the production of fish GHRH-like peptide and fish PACAP.

Chemical synthesis of a peptide of 38 or 45 amino acids in length is cumbersome and expensive. The novel cDNAs of the invention may be expressed in known expression systems thus providing a convenient and more efficient method for producing quantities of fish PACAP and/or fish GHRH-like peptide.

These peptides are useful either singly or in combination to enhance growth of fish by stimulation of endogenous growth hormone secretion.

The peptides may be administered to fish by injection, intraperitoneally or intramuscularly. For optimal growth enhancement, however, it is preferable that the peptides are administered to the fish continuously over a period of time. This may be done by administering the peptides in a slow release type of composition, such as implanted cholesterol pellets incorporating either or both peptides. Alternatively, either or both peptides may be incorporated into fish food and administered orally.

In accordance with a preferred embodiment, a cDNA encoding both GHRH-like peptide and PACAP is expressed to produce both peptides. To produce salmon GHRH-like peptide and PACAP, a DNA comprising nucleotides −39 to 668 of FIG. 1 is expressed, or a degeneracy equivalent or an effective portion or analog thereof. To produce catfish GHRH-like peptide and PACAP, a DNA comprising nucleotides −321 to 2181 of FIG. 2 is expressed, or a degeneracy equivalent or an effective portion or analog thereof.

Optionally, a single peptide may be produced by expression of a suitable cDNA. For salmon PACAP, a cDNA comprising nucleotides −51 to 357 of nucleotide sequence A of FIG. 10 may be employed.

A short cDNA containing GHRH, but not PACAP, is produced using PCR and specific primers. For example, primer 1 is made to the 5' untranslated region or any region 5' to the GHRH coding region and primer 2 is made to the 3' end of the GHRH coding region. A short cDNA containing PACAP, but not GHRH, of a type similar to that in FIG. 10, could be expressed for production of PACAP only.

The novel cDNAs of the invention may be expressed by methods known to those skilled in the art. The selected cDNA is ligated into a suitable expression vector downstream from a suitable promoter as described in Sambrook et al., (79) and in (32).

A translation initiating codon, ATG, and translation termination codons (TAA, TGA, or TAG) may be added if required. Suitable expression vectors include bacteriophage such as λgt11 or λZap II, plasmids such as pUC 12 and pUC 13, and animal viruses such as retroviruses and vaccinia viruses. Any promoter may be used which is suitable for expression in the selected host cell. Suitable host cells include animal cells such as Chinese hamster cell (CHO), rat GH4 pituitary cell, and adrenal medullary cell (PC12), bacterial cells or yeasts. A preferred promoter is that obtained from the fish growth hormone gene. The transformation of bacteria, yeast and animal cells is as described in [32] and Sambrook. The transformants are cultivated in the appropriate media. The expressed GHRH/PACAP precursor protein or mature peptide can be extracted from the culture as described by Parker and Sherwood (80). Active fractions from HPLC are detected by immunoassay using antisera to salmon GHRH or salmon PACAP. In addition, other known methods could be used for the GHRH and/or PACAP peptide purification.

Expression in neuroendocrine cells such as pituitary GH4 and adrenal medulla PC12 cells will give secretion of mature peptides [Steiner et al., (81)].

Further, both peptides will be secreted from the full length cDNA whereas the single peptides will be produced from the shortened cDNA. If expression is carried out in bacteria, precursor proteins will be secreted. The cells transfected or transformed with the DNA of the present invention can produce a large amount of the precursor protein or the mature peptides.

In accordance with a further embodiment of the invention, novel DNA constructs may be prepared containing the novel cDNAs of the invention; such constructs are useful to produce transgenic fish with increased production of GHRH-like peptide and/or PACAP resulting in increased growth.

Increased growth of transgenic fish transfected with a gene for fish GH has been demonstrated by Du et al. (69) and Zhu (70).

It has also been shown that mice transgenic for human GHRH had elevated levels of endogenous GH and showed enhanced growth [Hammer et al., (71)]. In contrast to GH-transgenic mice, all of the hGHRH-transgenic mice were fertile, suggesting that GHRH produces a more physiological effect on growth and reproduction.

In accordance with a further embodiment of the invention, a novel method is provided for producing enhanced growth of fish comprising transfecting the fish by introduction into fish eggs of a novel DNA of the invention, to produce expression of the DNA and production of GHRH-like peptide and/or PACAP whereby growth of the fish is enhanced.

This method of producing enhanced fish growth offers some advantages over direct administration of GHRH-like peptide and/or PACAP to fish. As indicated above, for optimal growth enhancement, exposure to the peptides may have to be continued over considerable periods of time, depending on the fish species. Repeated handling of fish for sequential treatments with peptides is, however, liable to cause stress syndrome; this risk can be avoided by the transfection method.

For transfection of fish with the novel DNAs of the invention, a selected DNA encoding the peptide or peptides to be expressed in the fish is operatively linked to a suitable upstream promoter and a suitable downstream transcription termination sequence ligated into a plasmid to form a DNA construct. The promoter and transcription termination sequence are ligated to the selected DNA by conventional methods, as will be understood by those skilled in the art.

Suitable promoters include RSV and TK. A promoter obtained from fish is preferred. Suitable fish promoters include SH, PRL and STH. The transcription termination sequence of the construct may be that associated with the selected DNA or may be another suitable transcription termination sequence.

A fish transcription termination sequence is preferred.

In accordance with an especially preferred embodiment of the invention, a DNA construct comprises a selected DNA in accordance with the invention encoding the peptide or peptides to be expressed in the fish, operatively linked to a fish growth hormone gene promoter and a fish growth hormone gene transcription termination sequence in a suitable plasmid such as pUC 18 or pUC 19. Such growth hormone promoters and transcription termination sequences are described in Du et al. (70).

This construct, having growth hormone gene promoter and transcription termination sequence, will be expressed in the pituitary which contains the endoproteases required for proper cleavage of the precursor proteins and where expression of the DNA will escape the control system operating on GHRH-like peptide expression and PACAP expression in brain tissue and which contains target receptors.

Suitable methods for introducing the construct into fish to produce transgenic fish are described by Hew et al. (75).

A preferred method is microinjection of the construct containing the selected DNA in accordance with the invention into fertilised, but not activated, teleost eggs. Fertilised teleost eggs can be injected relatively easily through the micropyle using a very fine glass needle (2–3 μm) [Fletcher et al. (76)]. Microinjection through the micropyle facilitates the procedure by 1) allowing for easier access to the egg cytoplasm and 2) providing a means of locating and introducing the vector in close proximity to the yet uncombined male and female pronuclei thereby increasing the chances of single cell genomic integration. Other methods of preparation of transgenic fish include introducing the vector by electroporation [Neuman et al., (77)] $CaCl_2$ precipitation, or lipofection [Felgner et al., (78)].

In accordance with a further embodiment of the invention, a method is provided for identifying a transgenic fish carrying a novel DNA construct in accordance with the invention. As described above, a DNA construct is created comprising a novel DNA coding for fish GHRH-like peptide and PACAP, or a shorter DNA coding for one of these peptides, ligated between a promoter and a transcription termination sequence (TTS).

When the promoter and TTS are obtained from a gene other than the PACAP/GHRH gene, fish transfected with such a DNA construct carry unique DNA sequences which may be used to identify the transgenic fish, as will be described.

The genome of a non-transgenic fish lacks any portion comprising GHRH/PACAP DNA, GHRH DNA or PACAP DNA joined to a heterologous promoter and/or a heterologous TTC.

If PCR amplification of a sample of fish DNA is carried out using a first primer which hybridises to a stretch of DNA spanning the junction between the heterologous promoter and the GHRH/PACAP DNA, or to a stretch of DNA spanning the junction between the GHRH/PACAP DNA and the heterologous TTS, and a second primer which hybridises to a portion of the GHRH/PACAP DNA insert, an amplified DNA is produced only from the DNA of transgenic fish.

As will be understood by those skilled in the art, a variety of primers may be made by conventional methods and used in this method for identification of transgenic fish, provided that one primer is generated to a unique site at the junction between the DNA insert and the heterologous flanking regions.

For analysis, DNA may be obtained from a variety of fish tissues, including blood and fin tissue.

Where a DNA construct is created using a promoter and TTS obtained from the PACAP/GHRH gene, the unique DNA sequences occurring at the junction between the vector and the homologous promoter or the homologous TTS may be similarly employed to identify transgenic fish, as these unique DNA sequences will not occur in non-transgenic fish. A suitable primer is made which hybridises to a stretch of DNA spanning the junction between the vector and homologous promoter or the vector and homologous TTS.

Comparison of Salmon GHRH-Like and PACAP Peptides with Mammalian Forms

The salmon GHRH-like peptide has sequence similarity not only to the mammalian GHRH, but also to the PRP region of the mammalian PRP/PACAP precursor. The processing sites in the salmon GHRH-like peptide suggest that it is processed to a free acid carboxy terminus like those of carp [11], rat [33,34] and mouse [35,36] GHRH peptides (FIG. 7). Salmon GHRH-like peptide is identical in length to the carp hypothalamic GHRH [11] and has 91% amino acid sequence identity (FIG. 7). There is only 40% sequence identity between the salmon GHRH-like peptide and human GHRH (FIG. 7). Even in mammals, the GHRH family is not highly conserved; rat [33,34] and mouse [35,36] GHRH have only 66% and 61% sequence identity to human GHRH, respectively. A comparison of the first 28 residues of the salmon GHRH-like peptide and human GHRH reveals a 57% sequence identity. The higher conservation of the amide terminus probably reflects the fact that only the first 29 amino acids of the carp and human GHRHs are required for full biological activity.

High sequence identity (59%) is also found in the first 28 amino acids between salmon GHRH-like peptide and the mammalian PRPs. No function has yet been shown for the mammalian PRP-29 molecule, but this molecule is processed and secreted from Chinese hamster cells that were transfected with an expression vector containing the human PACAP cDNA [37]. There is also some degree of amino acid sequence identity between salmon GHRH-like peptide and the big PRP region (48 residues) of the PRP/PACAP precursor from sheep (58%), human (56%) and rat (46%).

Analysis of the Untranslated Regions in the Salmon GHRH/PACAP cDNA

The 5' untranslated regions of two clones were different in size and sequence. The size of the 5' untranslated region was 39 bases in clone SS/RACE and 84 bases in clone SS/RACE 7 (FIG. 1). All clones containing the 5' untranslated region, including these longer clones and two shorter versions (see below), were identical from nucleotide positions −9 through −1, except for clone SS/RACE 7 which had an adenine at position −4 (FIG. 8). In common, the 5' untranslated regions have a adenine at position −3, which appears to be required for efficient translation [40,41]. Upstream of position −9, the 5' untranslated regions were completely different in all the clones. Differences in the 5' untranslated region are not unusual and the polymorphisms observed in this study may be due to differences in the regulation of the molecule. IGF I in the rat has different 5' untranslated regions which are connected to an identical precursor coding region [42]. An additional (ATG) codon is present in each of the 5' untranslated regions of two clones (SS/RACE 7 and CS/LIBb, FIG. 8), but translation from these sites would end at stop codons downstream. However, reinitiation at the next ATG codon would result in an in-frame precursor starting 16 amino acids downstream of the original initiator. Reinitiation in eukaryotic cells requires that the preceding open reading frame is short [41,43].

The 3' untranslated region is shorter in salmon GHRH/PACAP than in the mammalian precursors. Both clones SS/PCR 4 and SS/PCR 5 appeared to be complete because a homopolymeric (dA) tail was present with a putative polyadenylated signal 16 bp upstream. The polyadenylation signal, ATTAAA, is different from the ovine and human AGTAAA. Within the 3' untranslated region, the sequence AATC (624–631 bp, FIG. 9) is repeated in clone 4, occurs only once in clone 5, and is absent in the ovine and human precursors (FIG. 9). However, the 3' untranslated region of salmon GHRH/PACAP precursor is unique in that it has a high sequence identity (70%) to the mammalian forms (FIG. 9). Conservation between fish and mammals of 3' untranslated regions in other neuropeptide gene families are usually restricted to only a few motifs [44]. Considering the evolutionary distance between fish and mammals, approximately 400 million years, the high conservation of the 3' untranslated sequence is probably related to the function of the 3' untranslated region in interactions of the mRNA with proteins that affect mRNP structure and translational control [45].

Identification of a Short Precursor Containing only the PACAP Region

PCR products obtained from screening a chum salmon cDNA library with primers NMS2 combined with SK or KS, were assessed for GHRH/PACAP sequences. Six clones (CS/LIB) were identified that contained a shortened version of the GHRH/PACAP precursor. Four clones had a complete sequence from the NMS2 binding site through to the 5' untranslated region (FIG. 10). Two different 5' untranslated regions (CS/LIBa and CS/LIBb) were identified from these four clones (FIG. 10), The remaining two clones were truncated versions of the short precursor. In all CS/LIB clones the short precursor was formed by a deletion of 105 nucleotides at positions 234–338 the coding region for GHRH, leaving the PACAP coding region in a correct reading frame (compare FIG. 1 with 10). Five of the short precursor CS/LIB clones were found to contain an adenine at position 232 like that of the longer form of clone SS/RACE 7 (compare FIG. 1 with 10). This results in a change in the reading frame of the short precursor to a serine at amino acid position 78 (FIG. 10). Following position 78 in the short precursor, the reading frame then skips to position 114 of the longer GHRH/PACAP precursor and remains unchanged. Clone SS/RACE 2 has a guanine at position 232, which results in the triplet codon for glycine. Analysis of other clones from the RACE reaction (SS/RACE) also showed two clones that contained the same short precursor form as the CS/LIBa and b. Although these clones were identical in respect to the region deleted (bp positions 234–338), they had several nucleotide substitutions resulting in three amino acid changes (data not shown).

The site of the deletion, which corresponds exactly to exon 4 of the gene, is shown in FIG. 10. Exon 4 encodes $GHRH_{1-32}$ and three amino acids in the carboxy terminal portion of the cryptic peptide. The PACAP region is not shown, but is deduced from the fact that a specific primer made to PACAP (NMS3) was used to synthesize single stranded cDNA to obtain the short precursor.

The detection of a short precursor that contains only PACAP is of considerable interest in a functional sense. The fact that this short precursor form was obtained from both the RACE reaction of sockeye salmon mRNA and from the chum salmon cDNA library suggests it is not a cloning artifact. The short precursor form may have been due to problems of secondary structure in the mRNA during the reverse transcriptase reaction but, it is also possible that the short precursor was generated by differential post-transcriptional processing. Our partial sequence analysis of the salmon gene shows this short precursor may be the product of alternate processing of the mature mRNA (unpublished results). The region excised in the short cDNA precursor corresponds to a single exon containing the last 3 amino acids of the cryptic peptide and the first 32 amino acids of the GHRH-like molecule. The two exons encoding the cryptic peptide and PACAP are joined, resulting in a shorter mRNA that only codes for PACAP. Shorter transcript forms have been observed for another member of the glucagon superfamily; different transcriptional processing of secretin RNA results in the loss of exon three and a shorter precursor [46]. In the present study, cell specific processing of both precursors may have occurred in the brain since the source of the mRNA for the library and the RACE reaction was obtained from whole salmon brains. It is also possible that the shorter precursor is transcribed from a different gene with different regulatory elements.

Deduction of Polymorphism and Gene Copy Number

Four salmon GHRH/PACAP clones were identified that had nucleotide differences. The sequence heterogeneity of the coding and 3' untranslated regions between these two clones was greater than the expected error rate of Taq polymerase [47,48]. These clones may represent allelic polymorphisms or separate non-allelic genes. Salmonids are known to be tetraploid. Furthermore, an indication of more than one gene copy for the GHRH/PACAP precursor was observed in a Southern blot of sockeye salmon genomic DNA hybridized with a 355 bp probe which included the GHRH and PACAP coding regions and 91 bp of the 3' untranslated region. Restriction enzyme digests demonstrated that different allelic forms or genes are present.

Other members of the glucagon superfamily may be represented in bands that were easily removed by high stringency washes. In fish there are other examples in which differences in nucleotide sequence in the coding and 3' untranslated regions have been reported between two genes that code for the same hormone: melanin-concentration hormone [50,51], proopiomelanocortin [52], and corticotropin-releasing factor [44].

Expression of GHRH/PACAP mRNAs

Northern blots were done with a 588 bp probe that was amplified from the full length cDNA clone. Two bands were detected in sockeye salmon and chinook salmon brain poly(A)$^+$-rich mRNA, one band ranging from 2.5 to 2.8 Kb and the other from 0.7 to 1.0 Kb. The band width suggested that mRNAs of varying length were present.

The size of the larger salmon mRNA detected by Northern blot is in the same size range (3 Kb) as the rat, human, and ovine cDNAs. However, the 5' untranslated regions of the salmon GHRH/PACAP cDNAs are much shorter than the same region of other GHRH [35,53,54] and PACAP cDNAs [1,8,9] suggesting these salmon GHRH/PACAP clones may be incomplete. The length of the 5' untranslated region is unknown in any of the PACAP cDNAs, although it is at least 500–600 bp in rat and sheep.

The 3' untranslated region in the mammalian cDNAs is estimated to be 1400–1600 bp. This 3' untranslated region is quite different in length compared to 146 bp in the 3' untranslated region of the salmon. The rat VIP/PHI gene, which has high sequence identity to the PACAP gene, produces two different sizes mRNAs, a rare one with a 3' untranslated region of 100 base pairs and an abundant one of 800 bp [5]. The size of the small band (0.7–1.0 Kb) of salmon mRNA detected by Northern blot agrees with the size of the cDNA clone (0.73 Kb).

The length of the 5' and 3' untranslated regions is not important for use of the salmon cDNA for preparation of recombinant proteins or constructs for transgenic fish as this region may be supplied by the construct cassette.

The similarity between salmon GHRH-like peptide and the mammalian GHRHs is also indicated by the type of amino acid in positions known to be important for biological activity in mammalian GHRHs.

The N-terminal amino acid in the seven mammalian GHRHs reported to date is a hydrophobic residue, either Tyr or His (35,68). Substitution or modification of this initial Tyr or His in mammalian GHRHs has been shown to reduce potency drastically. The N-terminal amino acid of salmon, sturgeon and possibly catfish GHRH-like peptide is His (38,72). PACAPs, which also release GH, also have His as the N-terminal amino acid in both fish and mammals. In contrast, mammalian PRPs all have Asp as N-terminal amino acid.

As will be understood by those skilled in the art, DNA molecules comprising a number of nucleotide sequences are capable of encoding the precursor proteins and polypeptides of this invention, due to the degeneracy of the genetic code. The present invention includes both the nucleotide sequences specifically set out herein and all degeneracy equivalents or DNA molecules comprising nucleotide sequences which encode the same amino acid sequences as the specific nucleotide sequences.

The invention also includes portions of these nucleotide sequences, and analogs of these nucleotide sequences which encode polypeptides retaining the biological activity of the polypeptides described herein or encode precursor proteins which are precursors of polypeptides retaining the biological activity of the polypeptides described herein. These are referred to herein as "effective portions" or "effective analogs".

The amino acid sequences of the precursor proteins and polypeptides of the invention may be modified by conservative additions, deletions and/or substitutions while retaining the biological activity of these molecules, as will be understood by those skilled in the art. Such modified amino acid sequences are included within the scope of this invention and are referred to herein as "effective variants". Additionally, fragments or portions of the precursor proteins and polypeptides of the invention may retain biological activity and such fragments are included in this invention. They are referred to herein as "effective fragments".

It will be understood by those skilled in the art that variants or fragments of the polypeptides of the invention which retain biological activity may display higher or lower biological activity than the specifically described polypeptides.

The following examples are illustrative only and are not to be construed as limiting the invention.

EXAMPLES

Example 1

Sockeye Salmon cDNA 1.1 mRNA Purification and cDNA Synthesis

Sockeye salmon (*Oncorhynchus nerka*) were anesthetized with carbon dioxide and the brains were immediately excised and frozen in liquid nitrogen. Total RNA was isolated from sockeye salmon brains by extraction with acidic guanidinium thyiocyanate according to Chomczynski and Sacchi [27]. Poly $(A)^+$ mRNA was purified by oligo (dT) affinity chromatography (Pharmacia LKB Biotechnology). Double stranded cDNA was synthesized from 5 µg of poly $(A)^+$ mRNA using Stratagene's cDNA synthesis kit.

1.2 Amplification of cDNA

PCR samples were each prepared in a 100 µl volume containing 10 µl of double stranded cDNA, 100 pmol of primer CSC 33, 100 pmol of adaptor GAATTCT(dT) 36, 10 mM Tris-HCl (pH 8.3), 50 mM KCl, 0.01% gelatin, 0.05% NP 40, 0.05% Tween 20, 1.5 mM $MgCl_2$, 200 µM dNTPs and 2.5 units of Taq DNA polymerase (Perkin-Elmer Cetus). DNA was amplified using a step program of 1 cycle at 94° C. for 3 min, 55° C. for 2 min, and 72° C. for 4 min, followed by 29 cycles of 94° C. for 1 min 30 s, 55° C. for 2 min and 72° C. for 4 min (DNA Thermal Cycler, Perkin-Elmer Cetus). The last cycle had an 8 min extension at 72° C. Ten microliters of PCR product was removed and reamplified under the same conditions. PCR products were separated by electrophoresis on a 2.0% agarose gel (Bio 101) and the cDNA bands recovered by binding to Glassfog™ using MERmaid (Bio 101).

1.3 Amplification of the 5' End

We used the rapid amplification of cDNA ends (RACE) strategy designed by Frohman et al. [28], with minor modifications to amplify the 5'end. Two microliters of sockeye salmon poly $(A)^+$ mRNA (0.344 µg/µl) was mixed with 10 pmol of NMS 3 primer and 7 µl of DEPC treated water to a final volume of 10 µl, heated at 65° C. for 3 min then cooled rapidly on ice. Single stranded cDNA was made by adding 10 µl of reverse transcriptase solution (4 µl 5× BRL buffer (250 mM Tris-HCl, 375 MM KCl, 15 mM $MgCl_2$), 2 µl 0.1M DTT, 2 µl 10 mM dNTP's, 1 µl RNA guard (Pharmacia LKB Technology), and 1 µl M-MLV H RT (Superscript, BRL)) to the mRNA/primer mix and incubating for 2 h at 41° C. The reaction was stopped by heating to 75° C. for 10 min, then diluted to 500 µl with TE pH 7.5 and stored at 4° C. The primer was removed from the reaction mixture by centrifugation through a centricon-100 (Amicon) twice with 0.2× TE pH 7.5. First strand cDNA was vacuum concentrated to 12.5 µl, of which 10 µl was tailed with dATP at 37° C. for 5 min in 4 µl 5× BRL buffer, 4 µl MM dATP, 1 µl water and 1 µl TdT enzyme (BRL). The reaction mixture was heat denatured 5 min at 70° C. and diluted to 200 µl with sterile water. The remaining 2.5 µl of first strand cDNA was sham tailed (no enzyme) under the same conditions.

Polymerase chain reactions were done in 50 µl volumes containing 20 pmol of primer NMS 1, 20 pmol of adaptor #3(GGCTCGAGCCCGGGAATTCCG (Sequence ID NO: 19)), 5 pmol of adaptor #2(GGCTCGAGCCCGGG AATTCCG-dT$_{15}$ (Sequence ID NO: 18)), 1× Promega buffer (50 mM KCl, 10 mM Tris-HCl, 0.1% Triton X-100), 2.0 mM MgCl$_2$, 200 μM dNTP's, and 2.5 units of Taq DNA polyermase (Promega Corp., Madison, Wis.). In the first round of the PCR a 5 μl aliquot of dATP tailed cDNA was amplified using a step program for 30 cycles (DNA Thermal Cycler, Perkin-Elmer Cetus). In the first cycle the DNA was denatured at 94° C. for 3 min, annealed at 60° C. for 2 min and extended at 72° C. for 8 min. The following 29 cycles were 94° C., 58° C. and 72° C., all at 1 min intervals except for a final 8 min extension at 72° C. The PCR products were separated on a 1.5% agarose gel (SeaKem, FMC BioProducts) and the DNA bands electroeluted in dialysis tubing (Spect/Por, Spectrum Medical Ind., Inc.) with 1× TAE. Three microliters of this DNA was reamplified using primers NMS1 and adaptor #3 with a lower annealing temperature and more cycles (1 cycle at 94° C., 3 min; 55° C., 2 min; 72° C., 5 min; 41 cycles at 94° C., 1 min; 55° C., 1 min; 72° C. 1 min). The PCR amplified DNA was extracted, gel purified and electroeluted as previously.

Another strategy used to determine the 5' end of the GHRH/PACAP precursor, was to use the PCR to screen a chum salmon cDNA library prepared in lambda ZAP II (Stratagene, La Jolla, Calif.). To amplify the 5' end, primer NMS 1 in combination with primer SK or KS (Stratagene) were used in the first round of the PCR (1 cycle at 94° C. for 3 min, 45° C. for 2 min, 72° C. for 10 min; 41 cycles at 94° C. for 1 min, 45° C. for 2 min, 72° C. for 2 min; the last cycle had an 8 min extension at 72° C.). The PCR products were separated on a 2% agarose gel (Seakem) and the DNA bands retrieved as previously described. One fifth of this DNA was then reamplified with primers NMS2 and SK. The NMS2 primer was selected because it is internal to NMS1 and hence is specific for the region desired for amplification.

1.4 DNA Cloning

DNA obtained from the PCR was blunt end ligated into pBluescript II KS+ (Stratagene), which had been cut with EcoR V and dephosphorylated. The PCR products were blunt ended and kinased in 1× ligase buffer (50 mM Tris-HCl pH7.6, 10 mM MgCl$_2$, 5% polyethylene glycol-8000), 1 mM ATP and 200 μM dNTP's. Klenow polymerase (Pharmacia) was added and the reaction mixture incubated at 12° C. for 1 h, followed by the addition of T4 PNK (Pharmacia) and an incubation at 37° C. for 45 min. The reaction mixture was heat denatured at 75° C. for 15 min, then placed on ice. The cDNA was blunt end ligated into pBluescript II at 22° C. for 16–18 h by the addition 1 μl 5× ligase buffer, 2 μl 100 mM DTT, 0.5 μl 10 mM ATP, 0.5 μl vector and 1 unit of T4 ligase (BRL). Recombinant plasmids were identified by blue and white selection in XL-1 blue cells (Stratagene). Miniprep plasmid DNA was prepared by the alkaline hydrolysis method (29) and digested with Pvu II to identify plasmids with inserts. Recombinant plasmids were then screened by the PCR using primers CSC 33 and NMS 1 to identify clones containing the GHRH-like cDNA.

1.5 Sequencing

Single and double stranded cDNA inserts were sequenced by the chain termination method [30] using $^{35}$S- dATP (Dupont) and Sequenase Version 2.0 according to the manufacturer's instructions (US Biochemical Corp., Cleveland, Ohio).

1.6 Southern Blot

Sockeye salmon genomic DNA (24 μg) was digested with either Hae III, Hind III, Pst I, or EcoR I and electrophoresed on a 1% agarose gel. DNA was capillary transferred to Zeta probe nylon membrane (Bio-Rad) and prehybridized in aqueous buffer [31] at 60° C. for 3 h. The probe used in the hybridization was a 355 bp cDNA cut with MSE I and labelled with $^{32}$P-dCTP (Dupont) by random priming (5.6× $10^6$ cpm/ml). The filter was washed twice in 2× SSC/0.1% SDS for 15 min at room temperature, then twice in 1× SSC/0.1% SDS for 15 min at 60° C. and twice again in 1× SSC/0.1% SDS for 10 min at 60° C. prior to autoradiography.

1.7 Northern Blot

Northern blots and hybridization conditions were done according to Ausubel et al. [32]. Ten micrograms of salmon brain poly (A)$^+$ mRNA and 56 μg of salmon brain total RNA was electrophoresed on a formaldehyde denaturing agarose gel in 1× MOPS running buffer. RNA was capillary transferred with 10× SSC to a Zeta probe nylon membrane (Bio-Rad). The membrane was baked for 2 h at 80° C. and then prehybridized for 4 h at 42° C. with 15 ml of hybridization buffer (6× SSC/50% formamide/0.1% Tween 20/100 μg.ml$^{-1}$ denatured urchin sperm DNA) in a sealed plastic bag. The membrane was hybridized with a 588 bp cDNA probe 18–20 h at 42° C. in hybridization solution. The cDNA probe was made by amplification of the salmon GHRH/PACAP clone using primers SP1 (5'GGAATCATAATGCACTACAGTGTC 3' Sequence ID NO: 15) and NMS5 (5'GAACACAAGAGCGATCCACTGA 3' Sequence ID NO: 17), and labelled with $^{32}$P-dCTP by random priming.

Example 2

Synthesis and Characterization of Salmon GHRH and PACAP

Salmon GHRH and PACAP were synthesized on a Beckman 990 synthesizer using classical solid phase peptide synthesis techniques [73, 74]. In brief, these peptides were assembled on 4 g of a BocSer(Bzl) chloromethyl resin using Boc amino acids with the following side protecting groups: Lys(2-Cl-Z), Thr(Bzl), Glu(O-γ-cyclohexyl), Ser(Bzl), Asp (O-βcyclohexyl), Arg(Tos), His(Tos), and Tyr(2Br-Z). Hydrogen fluoride cleavage and deprotection at 0° C. in the presence of anisole as a carbocation scavenger was followed by (a) removal of the HF and unreacted anisole under vacuum, (b) treatment with anhydrous ethyl ether to remove residual HF, anisole, and their derivatives, and (c) extraction with aqueous HOAc and lyophilization to yield the crude peptidic preparations. Purification was accomplished using HPLC techniques. The composition of the final purified products was determined by amino acid analysis.

Example 3

Biological Activity of Salmon GHRH-Like Peptide and PACAP

Figure 11A:
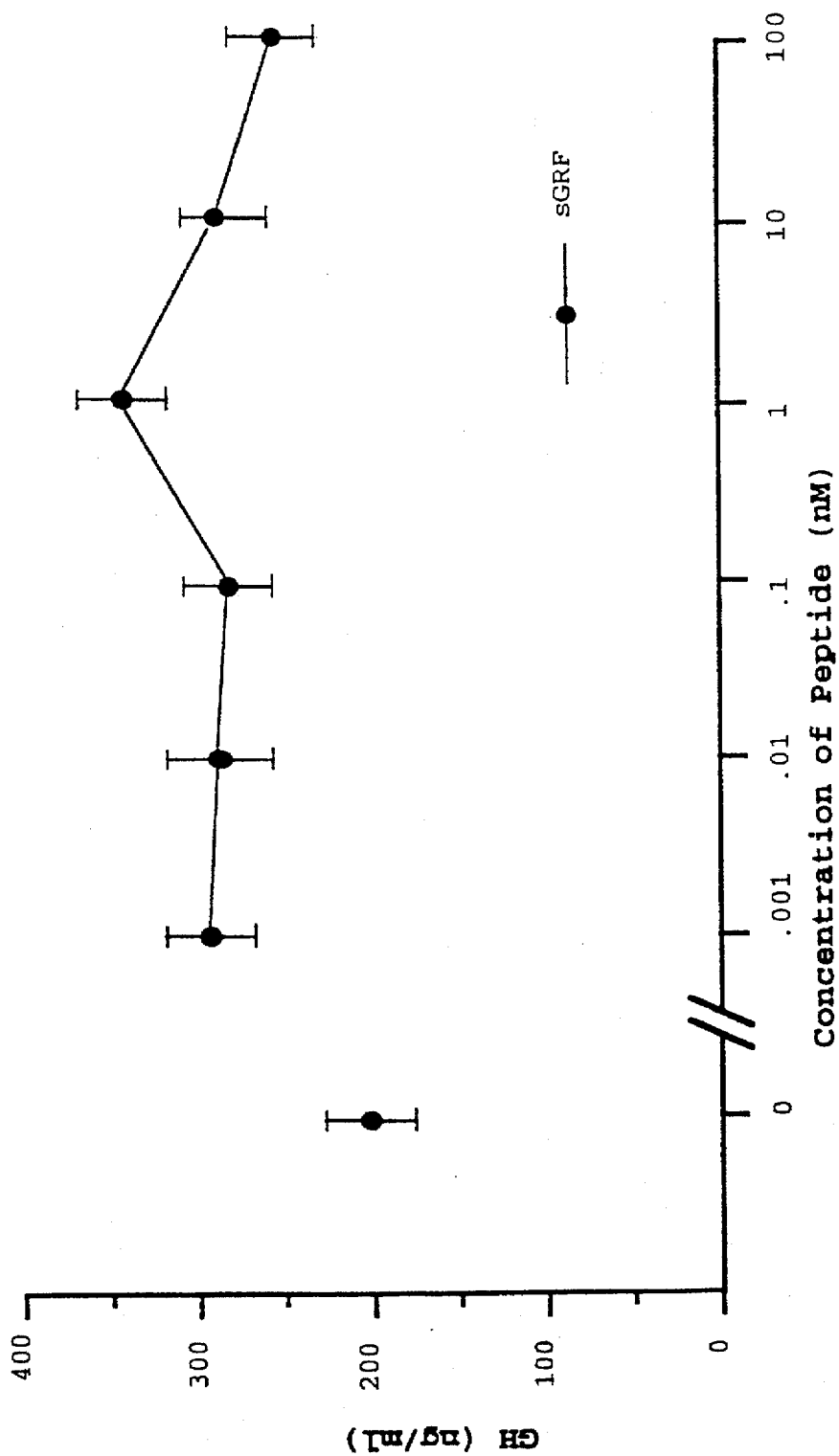
FIGS. 11A and B shows the GH releasing activity of salmon GHRH-like peptide (A) and salmon PACAP (B).
Figure 11B:
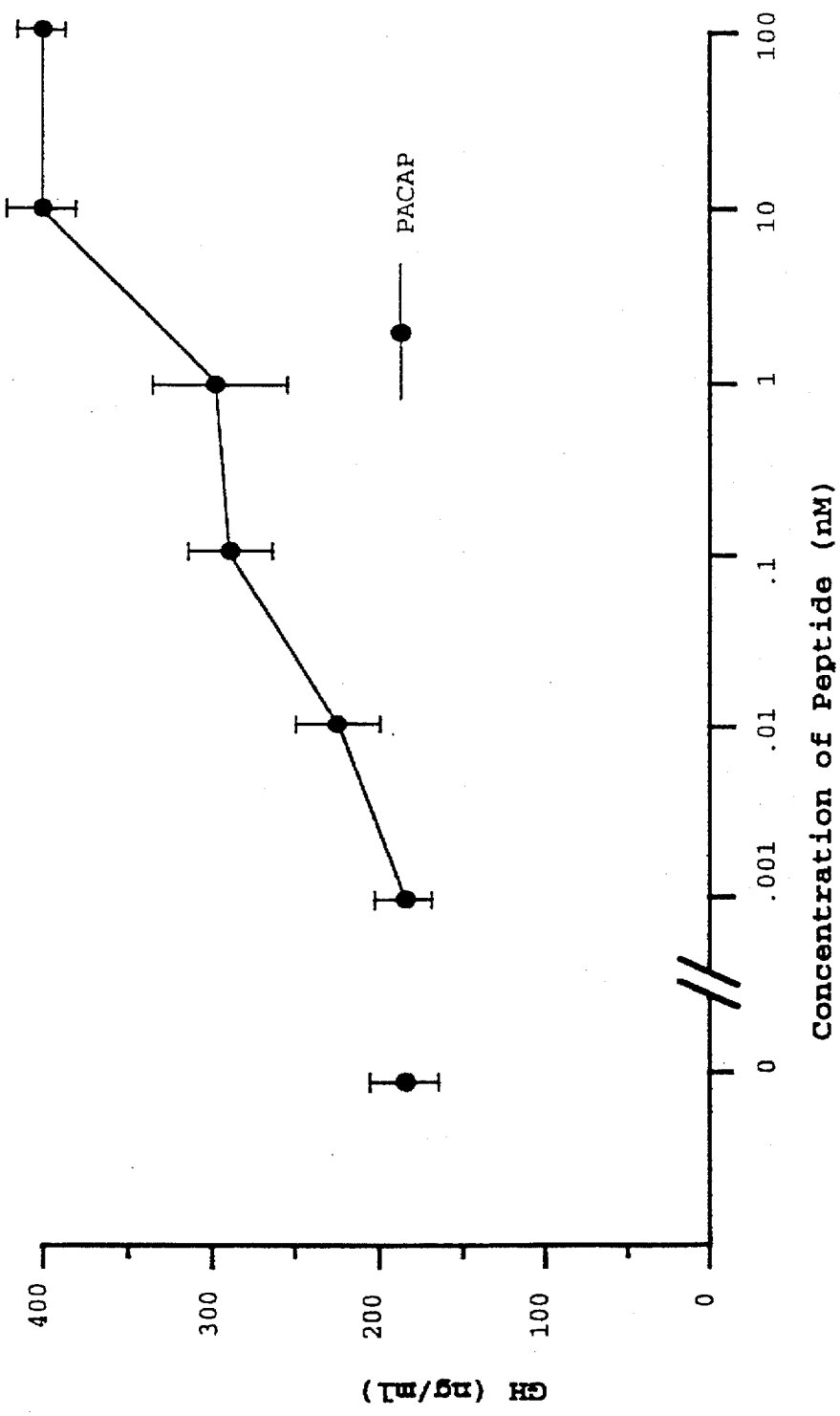
Figure 12:
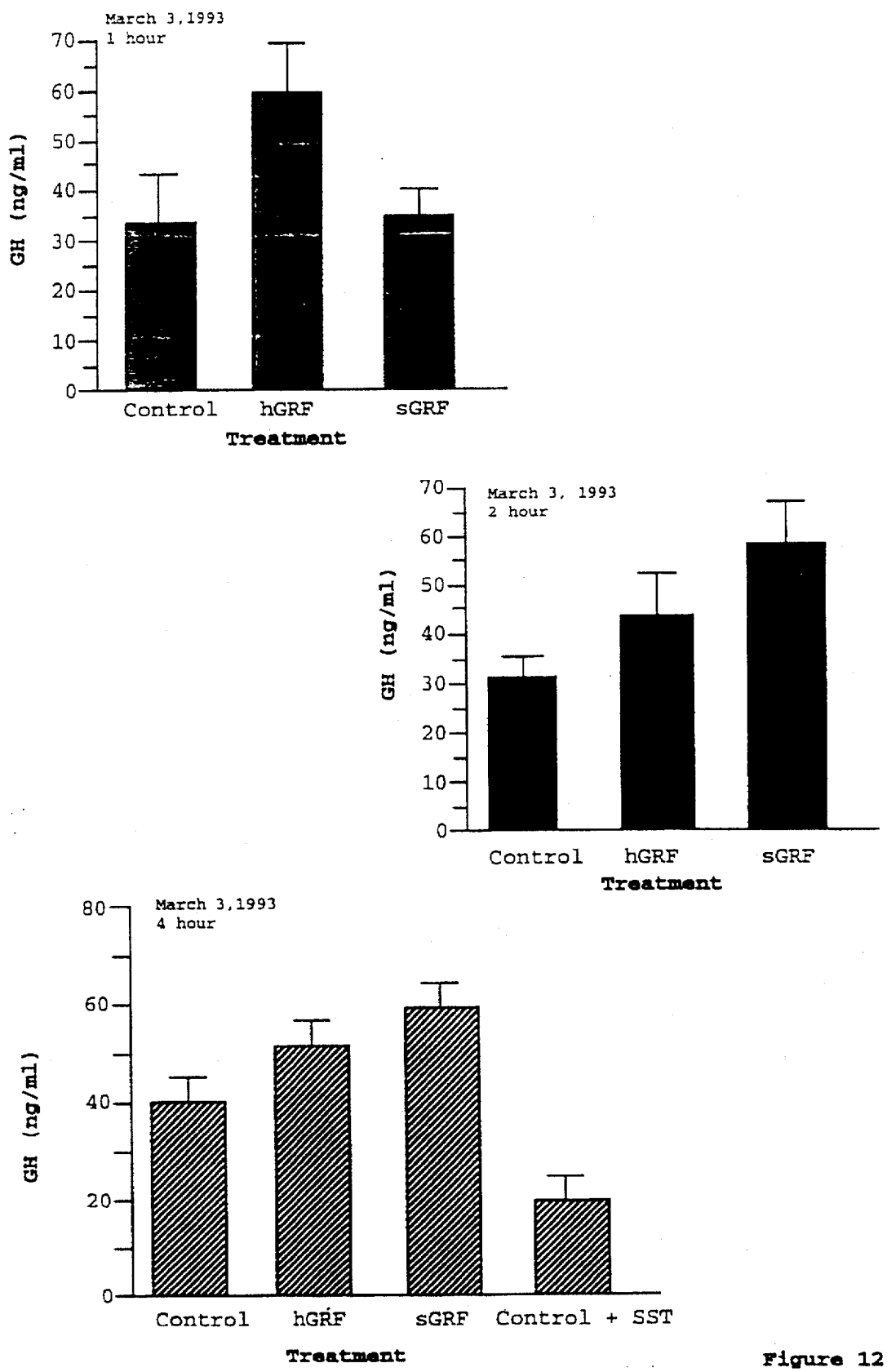
FIGS. 12A–C shows the GH releasing activity of salmon GHRH-like peptide compared with human $GHRH_{1-29}$ after 1 hour (A), 2 hours (B) or 4 hours (C) of incubation with salmon pituitary cells. SST=somatostatin.

Coho salmon pituitaries were removed and placed in sterile Hank's medium. Standard in vitro methods were used to prepare dispersed cells. Synthetic peptides were diluted in Hank's medium to the concentrations shown in FIG. 11. A concentration of $10^{-7}$M only was used in the time course study (FIG. 12). The peptides were added to the culture dishes on the 4th day of incubation. On the 5th day, the medium was collected and assayed for GH using a radioimmunoassay specific for salmon GH.

Example 4

Catfish cDNA 4.1 mRNA Purification and cDNA Synthesis

Brains were removed from Catfish (*Clarias macrocephalus*). The brains were immediately frozen in liquid nitrogen. The mRNA was isolated and cDNA synthesised as described for sockeye salmon in Example 1.1.

4.2 Preparation of a cDNA Library Plate Lysate

A cDNA library, prepared with Lambda Zap II (Stratagene) and Gigapack Gold packaging mix (Stratagene) was used to prepare a lysate with the following procedure.

Twelve plates (150×10 mm) of FRM bottom agar (5% NaCl, 2% MgCl$_2$—6H$_2$O, 10% NZ amine, 3% yeast extract, 2% casamino acids, 2% maltose and 14% agar) were covered with 8 mls FRM top agarose, 200 µl XL-1 cells and phage diluted to a density of 50,000 plaque forming units (pfu) per plate. The phage were grown (37°) until confluent lysis of the XL-1 cell lawn had occurred. Then, 10 ml of SM buffer was layered on top to swirl gently overnight. The next morning the SM buffer was removed and 5 ml of new SM buffer was added. After 3 hours of shaking, the SM buffer was removed, pooled with the initial wash and stored in a sealed glass bottle with a few drops of chloroform. The plate lysate was prepared from 10 ml of the SM buffer wash which was spun (10,000 g, 10 minutes) to pellet any bacterial material. After 10 µl RNaseA (Sigma, boiled, 10 mg/ml) and 25 µg of crude DNase I (Sigma) were added, the contents were vortexed well and incubated at 37° C. for 30 minutes. Following centrifugation (10,000 g, 10 minutes) the supernatant was removed and an equal volume of precipitating solution (2.5M NaCl, 20% polyethylene glycol) was added. The solution was allowed to precipitate on ice for 1.5 hr, then spun at 10 g for 20 minutes. The supernatant was removed; the pellet was hydrated in 400 µl of 1× proteinase K buffer (0.2% sodium dodecyl sulfate (SDS), 100 mM Tris pH 8, 150 mM NaCl, 10 mM EDTA). The hydrated pellet was combined with 20 mg proteinase K (BRL), incubated at 50° for 30 minutes, and extracted with two equal volumes of a solution containing one part of phenol(buffered) with one part of chloroform:isoamyl (24:1). These washes were then followed by two chloroform:isoamyl (24:1) washes. The mixture was spun (5,000 g, 5 minutes). The top layer was removed and 3M sodium acetate (final concentration of 0.3M) and 3 volumes of 100% ethanol were added.

4.3 Polymerase Chain Reaction (PCR) of Purified Library cDNA

The DNA amplification involved the nondegenerate primers, SP1, NMS3, and NMS4 (Sequence ID NO: 16), made against the salmon GHRH-PACAP cDNA sequence.

The first DNA amplification in the DNA Thermal Cycler (Perkin-Elmer Cetus), was in a 50 µl volume (2 µl cDNA, 5µl 10× Taq buffer (Promega), 8 µl 1.25 mM dNTP's (Pharmacia), 1 µl 20 µM SP 1 primer, 1 µl 20 µM NMS3 primer, 32.5 µl H20, and 0.5 µl Taq enzyme (Promega)). This solution was layered with 50 µl of mineral oil (Sigma), and cycled 35×, each cycle included steps at 94° for 1.5 minutes, 45° for 2 minutes, and 72° for 2.5 minutes with an extension period of 5 minutes and 16 seconds at 72°. Once the cycles were complete, the reaction mixture was combined with 50 µl chloroform (BDH), vortexed and spun at 10,000 g for 10 minutes. The top layer was removed and precipitated overnight with 5 µl of 3M sodium acetate and 2 volumes of 100% ethanol. The DNA solution was loaded onto an ethidium bromide stained 1.5% SeaKem gel and run until the bands were well separated. Four individual bands were cut out and separately electroeluted within dialysis bags (40 mAmps, 1.5 hours). This solution was precipitated overnight. The precipitated DNA was pelleted (10,000 g, 25 minutes), washed with 180 µl 75% ethanol and hydrated in 10 µl H$_2$O. This DNA solution was used for the second PCR amplification in a 50 µl reaction (10 µl DNA/H20, 5 µl 10× TAQ buffer, 8 µl 1.25nM dNTP, 1 µl 20 µM SP1 primer, 1 µl 20 µM NMS3 primer, 24.5 µl H$_2$O, and 0.5 µl TAQ DNA polymerase) using 35 cycles with steps of 94° (1.5 minutes), 50° (2 minutes), and 72°(2.5 minutes) plus an extension of 5 minutes and 16 seconds at 72°. Once completed, 5 µl of the reaction was removed directly from the PCR tube, combined with 5 µl of water and 2 µl of 6× loading buffer. The DNA mixture was loaded onto a 1.5 SeaKem gel (ethidium bromide stained) and electrophoresed one hour. Four sets of bands appeared under ultraviolet light but only three bands were considered large enough. Therefore, the three bands 2, 3, and 4, were cut out and electroeluted (45 m Amps, 1 hr) in dialysis bags.

4.4 DNA Cloning

Bands #2, #3, and #4, electroeluted and precipitated as described above, were cloned as described in Example 1.4.

4.5 Sequencing

Sequencing was done as described in Example 1.5.

4.6 cDNA Library Screening

For library screening the partial (393 bp) GHRH-PACAP cDNA clone was cut from KS-Bluescript with Not 1 (Pharmacia). The insert was electrophoresed on a 1.5 % gel, cut out and electroeluted, Library phage dilutions of $10^{-2}$, $10^{-4}$, $10^{-5}$, and $10^{-6}$ were individually (5 µl) combined in a 15 ml 2059 Falcon tube with 45 µl SM buffer and 100 µl XL-1 cells. The tubes were incubated 5 minutes at room temperature followed by 15 minutes at 37°. Molten (50°) FRM-agarose (3 ml) was added to the tube and the contents, poured over the FRM-agar plate (100×15 mm). The plates were incubated 10–12 hours at 37°.

For first round screening, two nylon membranes (DuPont) per plate were labelled "A" and "B". The A filters were laid on the agarose, for two minutes, then placed into 1 liter (L) of denaturing solution (1.5M NaCl, 0.5M NaOH) for 10 minutes. The filters were transferred to 1L of neutralizing solution (1.5M NaCl, 0.5M Tris-HCl pH 8), swirled 10 minutes and placed again in fresh neutralizing solution. The filters were transferred to 1L 2× SSC, swirled 5 minutes, transferred to fresh 2× SSC and agitated for another 5 minutes. The filters were removed and left to dry at room temperature. The B series membranes were put on the plates, left for 5 minutes, removed and placed in denaturing solution. The remaining procedure for the B filters was the same as for the A filters. All filters were combined, baked at 80° for 2 hours, and stored in a dessicator.

Prior to prehybridization the filters were placed one at a time into 6× SSC for 10 minutes. The 6× SSC was removed and 100 ml prehybridization solution (6×SSC, 5× Denhardt's solution, 0.5% SDS and 30 µg/ml boiled sea urchin DNA) was added and incubated with shaking for 4 hours at 50°. Labelling the GHRH probe followed the Vogelstein labelling method. To determine the labelling efficacy 2 µl was removed. The prehybridization solution was removed and 100 ml hybridization solution (6× SSC,+No. 5× Denhardt's solution 0.5% SDS, and 30 µg/ml boiled sea urchin DNA) was added to the filters. The labelled probe was boiled (10 minutes), quenched on ice, and combined with the hybridization solution. The filters were incubated overnight at 50°. The hybridization solution was decanted and stored at −20° for the second round. Filters were washed with increasingly higher stringency starting with 2×SSC-0.1%

SDS at 50° (45 min) and ending with 0.1×SSC-0.1% SDS at 65° (45 min). The filters were air dried and placed with film to develop for 7 days at −80°. Autoradiograms were then developed.

Postives were aligned against the original plate; the plaque of interest was cored and placed with 1.5 ml SM buffer and 20 µl chloroform. The mixture was left overnight at 4°.

4.7 In Vitro Excision

Once a single positive plaque was isolated, an in vitro excision was done to allow isolation of the plasmid cDNA. Combined were 200 µl XL-1 cells ($OD_{600}$=1.0), 200 µl lambda Zap II phage (isolated core), and 1 µl R408 helper phage. The mixture was incubated at 37° for 15 minutes and 2× YT media (5 ml) was added. The mixture was incubated 3 hours at 37° with vigorous shaking, heated to 70° for 20 minutes and spun 5 minutes at 4,000 g. The pBluescript supernatant was removed and stored at 4°.

4.8 Northern Blot

An agarose/formaldehyde gel (4.2 g agarose, 304.5 ml water, 35 ml 10× MOPS, 10.5 ml formaldehyde) was prepared for the Northern analysis. Thai catfish total RNA (20 µg) and a RNA ladder (4 µg) were loaded as molecular weight markers. The markers and another sample of total RNA (20 µg), Thai catfish poly A+mRNA (10 µg) and African catfish Poly A+mRNA (10 µg) were each mixed with 5 µl 10× MOPS, 8.75 µl 37% formaldehyde, and 25 µl formamide. The tubes were incubated 15 minutes at 55°. Loading buffer (10 µl) (1 mM EDTA, 0.25% Bromophenol blue, 0.25% Xylene Cyanol, and 50% glycerol) was added to the RNA and loaded onto the gel. The gel was run at 100 volts for 3 hours. The part of the gel with the two lanes of total RNA and RNA markers was cut from the rest of the gel and stained with an ethidium bromide solution (25 µl of 10 mg/ml in 500 ml) for 45 minutes. The remaining piece was washed several times with water (10 minutes each) and one wash of 10×SSC for 45 minutes.

A transfer pyramid was set up according to the Sambrook (1989) protocol using a Bio-Rad Zeta probe membrane and left overnight in 10× SSC. The pyramid was disassembled the next morning the membrane was air dried and baked at 80° for 2 hours. Once baked, the membrane was placed into a small bag with 10 ml Northern prehybridization solution (25 mM KPO4, 5× SSC, 10× Denhardts, 50% formamide, and 30 µg/ml sea urchin sonicated DNA) and incubated overnight at 40° C. The prehybridization solution was removed and 10 ml hybridization solution (same as prehybridization solution plus 5% dextran sulfate) and the probe were added. Hybridization was continued overnight at 40° C. Washes with stringency similar to those used for the filter lifts were used to clean the membrane. Once air dried, the filter was placed into a cassette, with amplifying screens, and stored at −80° overnight.

Example 5

Sturgeon cDNA

5.1 mRNA Purification and cDNA Synthesis

White sturgeon (*Acipenser transmontanus*) brains were excised and immediately frozen in liquid nitrogen. Total RNA was isolated from these brains by extracting with acidic guanidium thiocyanate, according to Chomczynski and Sacchi (27). Poly A+ mRNA was purified by oligo-dt affinity chromatography (Pharmacia LKB Biotechnology). Single stranded cDNA was synthesized from 2 µg of poly A+mRNA, using reverse transcriptase PCR technology and the sequence specific downstream primer, NMS 3.

5.2 Amplification of cDNA

PCR samples were each prepared in a 100 µl volume containing 10 µl of single stranded cDNA, 50 pmol of primer SP1, 50 pmol of primer NMS3, 2.5 units of Taq DNA polymerase (Promega), 1.5 mM $MgCl_2$, 200 µM dNTPs and 10 µl 10× Taq polymerase buffer (Promega). DNA was amplified using a step program of 1 cycle at 94° C. for 1.5 min., 55° C. for 2 min., and 72° C. for 6 min, followed by 35 cycles of 94° C. for 1.5 min, 54° C. for 2 min. and 72° C. for 3 min. (Perkin-Elmer Cetus). The last cycle had a 6 min. extension at 72° C. PCR products were separated by electrophoresis on a 1.5% agarose gel (FMC -SeaKem), recovered by electroelution and cloned and sequenced as in Example 1.4 and 1.5, respectively.

The present invention is not limited to the features of the embodiments described herein, but includes all variations and modifications within the scope of the claims.

TABLE I

AMINO ACID SEQUENCE IDENTITY OF CATFISH AND STURGEON GHRH/PACAP PRECURSORS COMPARED TO THE SALMON PRECURSOR

| | signal peptide | cryptic peptide | GHRH-like | PACAP-27 | PACAP-38 |
| --- | --- | --- | --- | --- | --- |
| salmon | 100 | 100 | 100 | 100 | 100 |
| catfish | 68 | 48 | 62 | 78 | 61 |
| sturgeon | — | 77 | 84 | — | — |

TABLE II

AMINO ACID SEQUENCE IDENTITY OF FISH GHRH/PACAP PRECURSORS COMPARED TO THE HUMAN PACAP PRECURSOR

| | signal peptide | cryptic peptide | GHRH-like/ PRP | PACAP-27 | PACAP-38 |
| --- | --- | --- | --- | --- | --- |
| human | 100 | 100 | 100 | 100 | 100 |
| salmon | 77 | 36 | 56 | 100 | 92 |
| catfish | 52 | 26 | 42 | 78 | 61 |
| sturgeon | — | 43 | 54 | — | — |

REFERENCES

1. Ohkubo, S., Kimura, C., Ogi, K., Okazaki, K., Hosoya, M., Onda, H., Miyata, A., Arimura, A., & Fujino, M. (1992) Primary structure and characterization of the precursor to human pituitary adenylate cyclase activating polypeptide, DNA Cell Biol. v. 11, pp. 21–30.

2. Hosoya, M., Kimura, C., Ogi, K., Ohkubo, S., Miyamoto, Y., Kugoh, H., Shimizu, M., Onda, H., Oshimura, M., Arimura, A., & Fujino, M. (1992) Structure of the human pituitary adenylate cyclase activating polypeptide (PACAP) gene, Biochim. Biophys. Acta v. 1129, pp. 199–206.

3. Bodner, M., Fridkin, M., & Gazes, I. (1985) Coding sequences for vasoactive intestinal peptide and PHM-27 peptide are located on two adjacent exons in the human genome, Proc. Natl. Acad. Sci. U.S.A. v. 82, 3548–3551.

4. Giladi, E., Shani, Y., & Gazes, I. (1990) The complete structure of the rat VIP gene, Mol. Brain Res. v. 7, pp. 261–267.

5. Lamperti, E. D., Rosen, K. M. & Villa-Komaroff, L. (1991) Characterization of the gene and messages for vasoactive intestinal polypeptide (VIP) in rat and mouse, Mol. Brain Res. v. 9, pp. 217–231.

6. Miyata, A., Arimura, A., Dahl, R. R., Minamino, N., Uehara, A., Jiang, L., Culler, M. D., & Coy, D. H. (1989) Isolation of a novel 38 residue-hypothalamic polypeptide which stimulates adenylate cyclase in pituitary cells, Biochem. Biophys. Res. Commun. v.164, pp. 567–574.

7. Miyata, A., Jiang, L., Dahl, R. D., Kitada, C., Kubo, K., Fujino, M., Minamino, N., & Arimura, A. (1990) Isolation of a neuropeptide corresponding to the N-terminal 27 residues of the pituitary adenylate cyclase activating polypeptide with 38 residues (PACAP38), Biochem. Biophys. Res. Commun. v. 170(2), pp. 643–648.

8. Kimura, C., Ohkubo, S., Ogi, K., Hosoya, M., Itch, Y., Onda, H., Miyata, A., Jiang, L., Dahl, R. R., Stibbs, H. H., Arimura, A., & Fujino, M. (1990) A novel peptide which stimulates adenylate cyclase: Molecular cloning and characterization of the ovine and human cDNAs, Biochem. Biophys. Res. Commun. v. 166, pp. 81–89.

9. Ogi, K., Kimura, C., Onda, H., Arimura, A., & Fujino, M. (1990) Molecular cloning and characterization of cDNA for the precursor of rat pituitary adenylate cyclase activating polypeptide (PACAP), Biochem. Biophys. Res. Commun. v. 173, p. 1271.

10. Chartrel, N., Tonon, M.-C., Vaudry, H., & Conlon, J. M. (1991) Primary structure of frog pituitary adenylate cyclase-activating polypeptide (PACAP) and effects of ovine PACAP on frog pituitary, Endocrinology v. 129, pp. 3367–3371.

11. Vaughan, J. M., Rivier, J., Spiess, J., Peng, C., Chang, J. P., Peter, R. E. & Vale, W. (1992) Isolation and characterization of hypothalamic growth-hormone releasing factor from Common carp, cyprinus carpio, Neuroendocrinology v. 56, pp. 539–549.

12. Parker D. B. & Sherwood, N. M. (1990) Evidence of a growth hormone-releasing hormone-like molecule in salmon brain, Oncorhynchus keta and O. kisutch, Gen. Comp. Endocrinol. v. 79, pp. 95–102.

13. Ackland, J. F., Wu, P., Bruhn, T. O., & Jackson, I. M. (1989) Partial purification and characterization of a novel growth hormone-releasing factor (GRF) from teleost brain related to the rat hypothalamic peptide, Peptides v. 10, pp. 15–19.

14. Arimura, A., Somogyvari-Vigh, A., Miyata, A., Mizuno, K., Coy, D. H., & Kitada, C. (1991) Tissue distribution of PACAP as determined by RIA: Highly abundant in the rat brain and testes, Endocrinology v. 129, pp. 4787–2789.

15. Köves, K., Arimura, A., Gorcs, T. G., & Somogyvari-Vigh, A. (1991) Comparative distribution of immunoreactive pituitary adenylate cyclase activating polypeptide and vasoactive intestinal polypeptide in rat forebrain, Neuroendocrinology v. 54, pp. 159–169.

16. Uddman, R., Luts, A., Arimura, A., & Sundler, F., (1991) Pituitary adenylate Cyclase-activating peptide (PACAP), a new vasoactive intestinal peptide (VIP)-like peptide in the respiratory tract, Cell Tissue Res. v. 265, pp. 197–201.

17. Vigh, S., Arimura, A., Köves, K., Somogyvari-Vigh, A., Sitton, J., & Fermin, C. D. (1991) Immunohistochemical localization of the neuropeptide, pituitary adenylate cyclase activating polypeptide (PACAP), in human and primate hypothalamus, Peptides v. 12, pp. 313–318.

18. Köves, K., Arimura, A., Somogyvari-Vigh, A., Vigh, S., & Miller, J. (1990) Immunohistochemical demonstration of a novel hypothalamic peptide, pituitary adenylate cyclase-activating polypeptide, in the ovine hypothalamus, Endocrinology v. 127, pp. 264–271.

19. Robberecht, P., Gourlet, P., Cauvin, A., Buscall, L., De Neef, P., Arimura, A., & Christophe, J. (1991) PACAP and VIP receptors in rat liver membranes, AM. T. Physiol. v. 260, pp. G97–G102.

20. Shivers, B. D., Gorcs, T. J., Gottschall, P. E., & Arimura, A. (1991) Two high affinity binding sites for pituitary adenylate cyclase-activating polypeptide have different tissue distributions, Endocrinology v. 128, pp. 3055–3065.

21. Gottschall, P. E., Tatsuno, I., Miyata, A., & Arimura, A. (1990) Characterization and distribution of binding sites for the hypothalamic peptide, pituitary adenylate cyclase-activating polypeptide, Endocrinology v. 127, pp. 272–277.

22. Lam, H.-C., Takahashi, K., Ghatei, M. A., Kanse, S. M., Polak, J. M., & Bloom, S. R. (1990) Binding sites of a novel neuropeptide pituitary-adenylate-cyclase-activating polypeptide in the rat brain and lung, Eur. J. Biochem. v. 193, pp. 725–729.

23. Schäfer, R., Schwarzhoff, R., Creutzfeldt, W., & Schmidt, W. E. (1991) Characterization of a guanosine-nucleotide—binding-protein-coupled receptor for pituitary adenylate-cyclase-activating polypeptide on plasma membranes from rat brain, Eur. J. Biochem. v. 202, pp. 951–958.

24. Suda, K., Smith, D. M., Ghatei, M. A., Murphy, J. K., Bloom, S. R. (1991)Investigation and characterization of receptors for pituitary adenylate cyclase-activating polypeptide in human brain by radioligand binding and chemical cross-linking, J. Clin. Endocrinol. Metab. v. 72, pp. 958–964.

25. Goth, M. I., Lyons, C. E., Canny, B. J., & Thorner, M. O. (1992) Pituitary adenylate cyclase activating polypeptide, growth hormone (GH)-releasing peptide and GH-releasing hormone stimulate GH release through distinct pituitary receptors. Endocrinology v. 130, pp. 939–944.

26. Culler, M. D. & Paschall, C. S. (1991) Pituitary adenylate cyclase-activating polypeptide (PACAP) potentiates the gonadotropin-releasing activity of luteinizing hormone-releasing hormone, Endocrinology v. 129, pp. 2260–2262.

27. Chomczynski, P. & Sacchi, N. (1987) Single-step method of RNA isolation by acid guanidinium thiocyanate-phenol-chloroform extraction, Anal. Biochem. v. 162, pp. 156–159.

28. Frohman, M. A., Dush, M. K. & Martin, G. R. (1988) Rapid production of full-length cDNAs from rare transcripts: amplification using a single gene-specific olignucleotide primer, Proc. Natl. Acad. Sci. U.S.A. v. 85, pp. 8998–9002.

29. Birnboim, M., (1983) A rapid alkaline extraction method for the isolation of plasmid DNA, Meth. Enzymol. v. 100, pp. 243–255.

30. Sanger, F., Nicklen, S., & Coulson, A. R. (1977) DNA sequencing with chain terminating inhibitors, Proc. Nail. Acad. Sci. U.S.A. v. 74, pp. 5463–5467.

31. Church, G. M. & Gilbert, W. (1984) Genomic sequencing, Proc. Natl. Acad. Sci. U.S.A. v. 81, pp. 1991–1995.

32. Ausubel, F. M., Brent, R., Kingston, R. E., Moore, D. D., Seidman, J. G., Smith, J. A. & Struhl, K. Current Protocols in Molecular Biology, Greene Publishing Associates and Wiley-Interscience, N.Y.

33. Spiess, J., Rivier, J., & Vale, W. (1983) Characterization of rat hypothalamic growth hormone-releasing factor, Nature v. 303, pp. 532–535.

34. Bohlen, P., Wehrenberg, W. B., Esch, F., Ling, N., Brazeau, P., Guillemin, R. (1984) Rat hypothalamic growth hormone-releasing factor: isolation, sequence analysis and total synthesis, Biochem. Biophys. Res. Commun. v. 125(3), pp. 1005–1012.

35. Frohman, M. A., Downs, T. R., Chomczynski, P., & Frohman, L. A. (1989) Cloning and characterization of mouse growth hormone-releasing hormone (GRH) complementary DNA: increased GRH messenger RNA levels in the growth hormone-deficient lit/lit mouse, Mol. Endocrinol. v. 3, pp. 1529–1536.

36. Suhr, S. T., Rahal, O. J., & Mayo, K. E. (1989) Mouse growth hormone-releasing hormone: precursor structure and expression in brain and placenta, Mol. Endocrinol. v. 3, pp. 1693–1700.

37. Okazaki, K., Kimura, C., Kosaka, T., Watanabe, T., Ohkubo, S., Ogi, K., Kitada, C., Onda, H., & Fujino, M. (1992) Expression of human pituitary adenylate cyclase activating polypeptide (PACAP) cDNA in CHO cells and characterization of the products, FEBS v. 298(I), pp. 49–56.

38. Guillemin, R., Brazeau, P., Bohlen, P., Esch, F., Ling, N., & Wehrenberg, W. (1982) Growth hormone releasing factor from a human pancreatic tumor that caused acromegaly, Science v. 218, pp. 585–587.

39. Coy, D. H., Murphy, W. A., & Lance, V. A. (1987) Observations on the chemistry and biology of growth hormone releasing factor in Growth Hormone, Growth Factors, and Acromegaly, (Lüdecke, K. & Tolis, G., eds) pp. 13–20, Raven Press, N.Y.

40. Kozak, M. (1986) Point mutations define a sequence flanking the AUG initiator codon that modulates translation by eukaryotic ribosomes, Cell v. 44, pp. 283–292.

41. Kozak, M. (1991) Structural features in eukaryotic mRNAs that modulate the initiation of translation, J. Biol. Chem. v. 266(30), pp. 19867–19870.

42. Lowe, W. L., Roberts, C. T., Lasky, S. R. & Roith, D. (1987) Differential expression of alternative 51 untranslated regions in mRNAs encoding rat insulin-like growth factor I, Proc. Natl. Acad. Sci. U.S.A. v. 84, pp. 8946–8950.

43. Hunt, T. (1985) False starts in translational control gene expression, Nature v. 316, pp. 580–581.

44. Morley, S. D., Schönrock, C., Richter, D., Okawara, Y., & Lederis, K. (1991) Corticotropin-releasing factor (CRF) gene family in the brain of the teleost fish *Catostomus commersoni* (white sucker): Molecular analysis predicts distinct precursors for two CRFs and one urotensin I peptide, Mol. Marine Biol. Biotechnol. v. 1, pp. 48–57.

45. Kwon, Y. K., & Hecht, N. B. (1991) Cytoplasmic protein binding to highly conserved sequences in the 31 untranslated region of mouse protamine 2 mRNA, a translated region of mouse protamine 2 mRNA, a translationally regulated transcript of male germ cells, Proc. Natl. Acad. Sci. USA v. 88, pp. 3584–3588.

46. Kopin, A., Wheeler, M. B., Nishitani, J., McBride, E. W., Chang, T.-M., Chey, W. Y. & Leiter, A. B. (1991) The secretin gene: Evolutionary history, alternative splicing, and development regulation, Proc. Natl. Acad. Sci. v. 88, pp. 5335–5339.

47. Tindall, K. R., & Kunkel, T. A. (1988) Fidelity of DNA synthesis by the *Thermus aquaticus* DNA polymerase, Biochemistry v. 27, pp. 6008–6013.

48. Saiki, R. K., Gelfand, D. H., Stoffel, S., Scharf, S. J., Higuchi, R., Horn, G. T., Mullis, K. B., & Erlich, H. A. (1988) Primer-directed enzymatic amplification of DNA with a thermostable DNA polymerase, Science v. 239, pp. 487–491.

49. Allendorf, F. W., & Thorgaard, G. H. (1984) Tetraploidy and the evolution of salmonid fishes, in Evolutionary Genetics of Fishes (Turner, J. ed) pp. 1–53, Plenum Press, N.Y.

50. Ono, M., Wada, C., Oikawa, I., Kawazoe, I., & Kawauchi, H., (1988) Structures of two kinds of mRNA encoding the chum salmon melanin-concentrating hormone, Gene v. 71, pp. 433–438.

51. Takayama, Y., Wada, C., Kawauchi, H., & Ono, M. (1989) Structures of two genes coding for melanin-concentrating hormone of chum salmon, Gene v. 80, pp. 65–73.

52. Nishizawa, T., Kitahara, N., Nanami, H., Hara, N., Kotake, C., Okazaki, H., Andoh, T., & Soma, G-I. (1984) Heterogeneity of 31 nontranslated regions in proopiomelanocortin (POMC) precursor mRNA of chum salmon Onchorynchus keta: polymorphism of the gene, Biochem. Biophys. Res. Commun. v. 122(2), pp. 556–562.

53. Gubler, U., Monahan, J. J., Lomedico, P. T., Bhatt, R. S., Collier, K. J., Hoffman, B. J., Bohlen, P., Esch, F., Ling, N., Zeytin, F., Brazeau, P., Poonian, M. S. & Gage, L. P. (1983) Cloning and sequence analysis of cDNA for the precursor of human growth hormone-releasing factor, somatocrinin, Proc. Natl. Acad. Sci. U.S.A. v. 80, pp. 4311–4314.

54. Mayo, K. E., Cerelli, G. M., Rosenfeld, M. G., & Evans, R. M. (1985) Characterization of cDNA and genomic clones encoding the precursor to rat hypothalamic growth hormone-releasing factor, Nature v. 314, pp. 464–467.

55. Larhammar, D., Söderberg, C., & Blomqvist, A. G. (1992) Evolution of the neuropeptide Y family of peptides, in Neuropeptide Y and Related Peptides (Wahlestedt, C., & Colmers, W. F., eds) Humana Press, (in press).

56. Canny, B. J., Rawlings, S. R., & Leong, D. A. (1992) Pituitary adenylate cyclase-activating polypeptide specifically increases cytosolic calcium ion concentration in rat gonadotropes and somatotropes, Endocrinology v. 130, pp. 211–215.

57. Luo, D., McKeown, B. A., Rivier, J., & Vale, W. (1990) In vitro responses of rainbow trout (Oncorhynchus mykiss) somatotrophs to carp growth hormone-releasing factor (GRF) and somatostatin, Gen. Comp. Endocrinol. v. 80, pp. 288–298.

58. Heinrich, G., Gros, P., & Habener, J. F. (1984) Glucagon gene sequence. J. Biol. Chem. v. 259, pp. 14082–14087.

59. Bell, G. I. (1986) The glucagon superfamily: precursor structure and gene organization, Peptides v. 7(I), pp. 27–36.

60. Parker, D. S., Raufman, J-P., O'Donohue, T. L., Bledsoe, M., Yoshida, H. & Pisano, J. J. (1984) Amino acid sequences of helospectins, new members of the glucagon superfamily, found in gila monster venom, J. Biol. Chem. v. 259(19), pp. 11751–11755.

61. Hoshino, M., Yanaihara, C., Hong, Y-M., Kishida, S., Katsumaru, Y., Vandermeers, A., Vandermeers-Piret, M-C., Robberecht, P., Christophe, J. & Yanaihara, N. (1984) Primary structure of helodermin, a VIP-secretin-like peptide isolated from Gila monster venom, FEBS v. 178(2), pp. 233–239

62. Rivier, J, Spiess, J., Thorner, M. & Vale, W. (1982) Characterization of a growth hormone-releasing factor from a human pancreatic islet tumour, Nature v. 300, pp. 276–278.

63. Frohman, L. A. & Jansson, J.-O. (1986) Growth hormone-releasing hormone, Endocr. Rev. v. 7, pp. 223–253.

64. Barinaga, M., Yamonoto, G., Rivier, C., Vale, W., Evans, R. & Rosenfeld, M. G. (1983) Transcriptional regulation of growth hormone gene expression by growth hormone-releasing factor, Nature v. 306, pp. 84–85.

65. Frawley, L. S. & Hoeffler, J. P. (1988) Hypothalamic peptides affect the ratios of GH and PRL cells: Role of cell division, Peptides v. 9: pp. 825–828.

66. Mayo, K. E., Cerelli, G. M., Lebo, R. V., Bruce, B. D., Rosenfeld, M. G. & Evans, R. M. (1985) Gene encoding human growth hormone-releasing factor precursor: Structures, sequence, and chromosomal assignment, Proc. Natl. Acad. Sci. USA v. 62: p. 63

67. Gick, G. G., Zeytin, F. N., Brazeau, P., Ling, N. C., Esch, F. S. & Bancroft, C (1984) Growth hormone-releasing factor regulates growth hormone mRNA in primary cultures of rat pituitary cells, Proc. Natl. Acad. Sci. USA v. 81: p. 1553.

68. Guillemin, R. (1986) The Sherrington Lectures XVIII. Hypothalamic Control of Pituitary Functions. The Growth Hormone Releasing Factor. Liverpool University Press, Liverpool, U.K., pp 1–73.

69. Du, S. J., Gong, Z., Fletcher, G. L., Shears, M. A. & Hew C. L. (1992) Growth hormone gene transfer in Atlantic salmon: Use of fish antifreeze/growth hormone chimeric gene construct, In Transgenic Fish (ed. C. L. Hew & G. L. Fletcher) World Scientific Publ. Co., Singapore, pp. 176–189.

70. Zhu, Z. (1992) Generation of fast growing transgenic fish: Methods and mechanisms, In Transgenic Fish (ed. C. L. Hew & G. L. Fletcher) World Scientific Publ. Co., Singapore, pp. 92–119.

71. Hammer, R. E., Brinster, R. L., Rosenfeld, M. G. Evans, R. M. and Mayo, K. E. (1985) Expression of human growth hormonereleasing factor in transgenic mice results in increased somatic growth. Nature v. 315: pp. 413–416.

72. Ling, N., Baird, A., Wehrenberg, W. B., Ueno, N., Munegumi, T., Chiang, T.-C., Regno, M. & Brazeau, P (1984) Synthesis and in vitro bioactivity of human growth hormone-releasing factor analogs substituted at position-1, Biochem. Biophys. Res. Communic. v. 122: pp. 304–310.

73. Stewart, J. M., Young, J. D. (1984) Solid Phase Peptide Synthesis, ed. 2., Pierce Chemical Co., Rockford.

74. Merrifield, R. B. (1963) Solid phase peptide synthesis. I. The synthesis of a tetrapeptide, J. Am. Chem. Soc. v. 85: pp. 2149–2154.

75. Hew, C. L. and Fletcher, G. L. (Eds), 1992, *Transgenic Fish,* World Scientific Press, N.J. at pp. 1–274.

76. Fletcher, G. L., Shears, M. A., King, M. J., Davies, P. L. and Hew C. L.(1988), Evidence for antifreeze protein gene transfer in Atlantic salmon (*Salmo salar*), CAN. J. Fish aquat Sci. v. 45, pp. 252–357.

77. Neuman E., Schaefer-Ridder M., Wang Y. and Hofschneider P. H. (1982), Gene transfer into mouse lyoma cells by electroporation in high electric fields. EMBO J. v. 1(7), pp. 841–845.

78. Felgner P. L., Gadek T. R., Holm M., Roman R., Chan H. W. and Danielson M. (1987), Lipofection: A highly efficient, lipid-mediated DNA transfection procedure. Proc. Natl. Acad. Sci., v. 84, pp. 7413–7417.

79. Sambrook J., Fritsch E. F., and Maniatis T., Molecular cloning, a laboratory manual, 2nd edition. Cold Spring Harbor Laboratory Press, (1989).

80. Parker D. B. and Sherwood, N. M., (1990) General and Comparative Endocrinolgy . . . v. 79, pp. 95–102.

81. Steiner D. F., Smeekens S. P., Ohagi S. and Chan S. J., (1992) J. Biol. Chem. v. 267, pp. 23435–23438.

---

---

We claim:

1. A purified and isolated nucleic acid molecule encoding a fish pituitary adenylate cyclase activating peptide and a fish growth hormone releasing hormone, the nucleic acid molecule comprising a nucleotide sequence selected from the group consisting of:
 (a) nucleotides 1 to 707 of SEQ. I.D. NO. 1;
 (b) nucleotides 40 to 561 of SEQ. I.D. NO. 1;
 (c) nucleotides 1 to 2502 of SEQ. I.D. NO. 2; and
 (d) nucleotides 322 to 864 of SEQ. I.D. NO. 2.

2. A purified and isolated nucleic acid molecule according to claim 1 wherein the nucleotide sequence comprises nucleotides 40 to 561 of SEQ. I.D. No. 1.

3. A purified and isolated nucleic acid molecule according to claim 1 wherein the nucleotide sequence comprises nucleotides 322 to 864 of SEQ. I.D. No. 2.

4. A purified and isolated nucleic acid molecule encoding a peptide having an amino acid sequence selected from the group consisting of:
 (a) Seq. I.D. No. 6;
 (b) Seq. I.D. No. 7;
 (c) Seq. I.D. No. 11.

5. A purified and isolated nucleic acid molecule according to claim 4 wherein the encoded peptide has an amino acid sequence as set forth in Seq. I.D. No. 6.

6. A purified and isolated nucleic acid molecule according to claim 4 wherein the encoded peptide has an amino acid sequence as set forth in Seq. I.D. No. 7.

7. A purified and isolated nucleic acid molecule according to claim 4 wherein the encoded peptide has an amino acid sequence as set forth in Seq. I.D. No. 11.

8. A vector including a nucleic acid molecule according to claim 4.

9. A host cell including a vector according to claim 8.

10. A method for producing at least one peptide selected from the group consisting of:
 (a) a fish pituitary adenylate cyclase activating peptide; and
 (b) a fish growth hormone releasing hormone peptide, the method comprising the steps of:
  providing a host cell according to claim 9,
  culturing said cell in a growth medium under conditions such that express said peptide; and
  recovering said peptide.

11. A purified and isolated nucleic acid molecule encoding a fish pituitary adenylate cyclase activating peptide and having a nucleotide sequence selected from the group consisting of:
 (a) nucleotides 424 through 537 of Seq. I.D. No. 1;
 (b) nucleotides 424 through 504 of Seq. I.D. No. 1;

(c) nucleotides 709 through 325 of Seq. I.D. No. 2; and (d) nucleotides 709 through 789 of Seq. I.D. No. 2.

12. A nucleic acid molecule according to claim 11 wherein the molecule has a nucleotide sequence as set forth in nucleotides 424 through 537 of Seq. I.D. No. 1.

13. A nucleic acid molecule according to claim 11 wherein the molecule has a nucleotide sequence as set forth in nucleotides 424 through 504 of Seq. I.D. No. 1.

14. A nucleic acid molecule according to claim 11 wherein the molecule has a nucleotide sequence as set forth in nucleotides 709 through 825 of Seq. I.D. No. 2.

15. A nucleic acid molecule according to claim 11 wherein the molecule has a nucleotide sequence as set forth in nucleotides 709 through 789 of Seq. I.D. No. 2.

16. A vector including a nucleic acid molecule according to claim 11.

17. A host cell including a vector according to claim 16.

18. A method for producing a fish pituitary adenylate cyclase activating peptide comprising the steps of:

providing a host cell according to claim 17;

culturing said cell in a growth medium under conditions such that express said peptide; and recovering said peptide.

19. A purified and isolated nucleic acid molecule encoding a growth hormone releasing hormone, the nucleic acid molecule comprising a nucleotide sequence selected from the group consisting of:

(a) nucleotides 283 through 417 of SEQ. I.D. No. 1;

(b) nucleotides 283 through 366 of SEQ. I.D. No. 1;

(c) nucleotides 568 through 702 of SEQ. I.D. No. 2;

(d) nucleotides 181 through 315 of SEQ. I.D. No. 3; and (e) nucleotides 181 through 264 of SEQ. I.D. No. 3.

20. A nucleic acid molecule according to claim 19 wherein the molecule has a nucleotide sequence as set forth in nucleotides 283 through 417 of SEQ. I.D. No. 1.

21. A nucleic acid molecule according to claim 19 wherein the molecule has a nucleotide sequence as set forth in nucleotides 283 through 366 of SEQ. I.D. No. 1.

22. A nucleic acid molecule according to claim 19 wherein the molecule has a nucleotide sequence as set forth in nucleotides 568 through 702 of SEQ. I.D. No. 2.

23. A nucleic acid molecule according to claim 19 wherein the molecule has a nucleotide sequence as set forth in nucleotides 181 through 315 of SEQ. I.D. No. 3.

24. A nucleic acid molecule according to claim 19 wherein the molecule has a nucleotide sequence as set forth in nucleotides 181 through 264 of SEQ. I.D. No. 3.

25. A vector including a nucleic acid molecule according to claim 19.

26. A host cell including a vector according to claim 25.

27. A method for producing a fish growth hormone releasing hormone peptide comprising the steps of:

providing a host cell according to claim 26;

culturing said cell in a growth medium under conditions such that express said peptide; and recovering said peptide.

* * * * *

SEQUENCE LISTING ( 1 ) GENERAL INFORMATION:

( i i i ) NUMBER OF SEQUENCES: 49

( 2 ) INFORMATION FOR SEQ ID NO: 1:

( i ) SEQUENCE CHARACTERISTICS:
        ( A ) LENGTH: 707 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 1:

```
GACATCCAGC   TTGTCTCTCC   ACACGGTAAT   AGCAGGACAA   TGTCTAGTAA   AGCGACTTTA        60
GCCTTACTCA   TCTATGGAAT   CATAATGCAC   TACAGTGTCT   ACAGCTCACC   TCTCGGCTT        120
AACTATCCTA   ACCTTAGACT   TGAAAATGAG   GTTTATGACG   AGGATGGGAA   TTCGTTACCG       180
GCCTTGGCTT   TTGACAGCGA   TCAAATTGCT   ATAAGAAGTC   CCCCGTCTGT   GGCTGACGAT       240
TTATACACTT   TATACTACCC   ACCGGAGAAA   GGAACGAAA    GGCATGCAGA   CGGAATGTTT       300
AATAAAGCCT   ACAGGAAAGC   GCTGGGTCAG   TTATCAGCAA   GAAAATATCT   TCATTCTCTG       360
ATGGCAAAGC   GTGTAGGTGG   AGGGAGCACC   ATGGAAGACG   ACACAGAGCC   TCTGTCAAAG       420
CGACATTCGG   ATGGGATCTT   CACAGATAGC   TACAGCCGCT   ACCGAAAGCA   AATGGCAGTC       480
AAGAAATACC   TGGCGGCAGT   CCTTGGGAAA   AGGTATAGAC   AGAGATATAG   AAACAAAGGA       540
CGCCGGCTAG   GCTATCTGTA   GCGTTGCTAA   CCCAAACTAC   CATGTGTGTA   CAGCCCAGAT       600
```

-continued

| | | | | | |
|---|---|---|---|---|---|
| CAAGTCATTT | TGAGATAACT | GAACAATCAA | TCAGTGGATC | GCTCTTGTGT | TCTTTAAACA | 660 |
| TGTATTTATG | TATGAAGTAA | AGCCATTAAA | ATGAATATTT | TGATAAT | | 707 |

(2) INFORMATION FOR SEQ ID NO: 2:

(i) SEQUENCE CHARACTERISTICS:
        (A) LENGTH: 2502 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

| | | | | | |
|---|---|---|---|---|---|
| GACGAATCTC | ATCGACAATT | TTTTTTTTG | TTCGCAGAAG | GCTATTATTT | TATTTTTTC | 60 |
| ATTTGTTTGT | TTTTAGAAGC | GGCTTATTGT | ATAAAAGTCA | AAGGCGGCTT | ATCAGGACGA | 120 |
| GCCCATCAGG | AATATCGGCG | GTGGCGCTCA | GAGAAGAGGT | GCCGAGAGAA | AGATTACCTC | 180 |
| GTCTCTCTCT | TTCTCTCCCT | CTCTCCTTCT | CTCCCTCTGT | CTCTCTTTCA | CTCACACATA | 240 |
| CACACATAGA | CACACACACA | CGCTCAGCAG | CCGCACCCGA | AGCCCGTCCG | CAGCCTCGCT | 300 |
| CTCTGACCAA | ACTGCCGTAG | CATGGCCAAA | TCTAGTAGAG | CTACTTTGGC | TCTGCTCATC | 360 |
| TACGGGATCT | TAATGCGCTA | CAGCCAATGC | ACACCATCG | GAATGGGCTT | CCCCAATATG | 420 |
| AGGCTAGACA | ACGACGTGTT | CGGGGACGAG | GGAAACTCGT | TAAGTGAGCT | GTCCTACGAG | 480 |
| CCGGACACGA | TGAGCGCGCG | CAGTCGTCCA | GCCCTCCCTG | AAGACGCATA | CACACTGTAC | 540 |
| TATCCGCCCG | AGAGAAGAGC | CGAAACGCAT | GCAGACGGAT | TGTTAGATAG | AGCCTTGAGG | 600 |
| GACATCCTGG | TTCAGTTATC | AGCCCGAAAA | TATCTGCATT | CTCTGACGGC | AGTTCGCGTA | 660 |
| GGTGAGGAAG | AAGAGGATGA | AGAGGACTCG | GAGCCACTGT | CGAAGCGCCA | CTCGGACGGC | 720 |
| ATTTTCACGG | ACAGCTACTC | GCGCTACCGG | AAACAAATGG | CCGTAAAAAA | ATACCTTGC | 780 |
| AGCAGTGCTG | GGAAGAAGGT | ACAGACAGAG | CGGGCCGCGA | ATTCGCGCCG | CATTGGTTGT | 840 |
| ACCATCAGTT | TGGACGGGCA | TTAGGGACAC | TGTCATAATC | ACTCCGGAGA | AGAGAGGAAA | 900 |
| AAGGTATTAA | TTGGAGTTAC | CCAGGTCACG | TCTCTGTGAA | GTGCCTGCTG | AAGTGAACAA | 960 |
| GCAGTTGAAT | GAAACCCATG | TGGATTTGCT | CATTTCTGAT | GTCCTGAGAC | ACCAAATTGG | 1020 |
| TGCAAAGATT | GGTGAGGTTG | TGCAGAATCT | GTATTCCCAG | AATGGATTTC | ATCTGGCTTG | 1080 |
| GAGCTTGGGT | CATCGTGTCA | AGGGACACCT | GGCAAGCATG | GTTGAGCCTG | CAACTATTAA | 1140 |
| GTTGCATCAG | CTGCTGCTGC | TTACTCTGCC | TGGAACTCCC | ATCTTAACTA | TGGAGATGAA | 1200 |
| ATTGGACTAA | AGGATGAGGA | TTCTGTGTAT | CCAGCGATGT | TGGATTTGTC | AAATGAGACT | 1260 |
| GAAAAGGCTG | GTGTAGAGGA | CAGAATCTCT | ACGCACTTTC | TTCAAGGCAT | GTGAGTGACC | 1320 |
| TCCGAGGAAA | AGAGCGATCC | CTTCAGCATG | GAGATTATGT | GCCTCTGTAC | AACGACACCA | 1380 |
| GAGTTCTTGC | ATACTTGCGC | TCATGGGACC | AGAGTGAACG | CTACAGAGTT | GCATTAAACT | 1440 |
| GGGGTATAGA | TCAAGCAACT | CTGCCATTGA | CCAACGAATT | GCTTCCTGAG | GAAAGCCAAG | 1500 |
| GTTGTAGTTA | GTACTACTGA | AAAACTGAAA | CCTGATGAGT | TTGTTAACTT | GGCCGAATTA | 1560 |
| AGGCTGGAGT | CACAACAGGC | TGTTCTGCTT | AAATTCCCTT | ATGTTGCGTA | AATGGGGGCT | 1620 |
| CTTCTGCATC | TCTTTTAGAC | GAAGATATAC | AAGTTGTTGT | TGTTGGGTAA | TGTTACATGT | 1680 |
| TATAAATATT | GTTACAGTCA | TTGTGCTGAA | TGGGTAGTAA | AATAAAAATA | CAGTAATTAC | 1740 |
| AGTATAGAGT | ATACAAACTG | TGCACAATCA | AAGGTCAGGT | CCAATTGTTT | TATTAAGTCC | 1800 |
| CCCCATATAT | ATTTTTTAAA | TCCTTATTTA | AAAAAACATT | CCAGGTTTCA | GCCTATTTAA | 1860 |

```
AATGTTGTGG  TTGCAATGCG  GTTTTGTGAT  TGTGTAAAAT  GTCAGTTTGA  TCTGTTGTTG      1920

GCAAGAGCGA  ATTCGCGGCC  GAAAAAAAA   CAAAACAAA   CCCTTGACCC  TTGCTAATTT      1980

TCCCTGACTT  CGAAATTTTC  CCTGACTTGA  CTTTTACCCA  TCCATGAAAC  TGACTGCAGC      2040

CCTGGGCCCA  GACCCTCCTA  CACCTTAACC  CCATAACATT  CAGCTCCCCC  ACCCGTCTCT      2100

GCATGCGCCA  CTGAGGCCTT  GTGCGCTGCT  TCTATCTCCA  TTCGAGCTTG  TGCGCTCTTA      2160

CAAATCCCTC  TGCGATGTCA  CAGAAGTAGG  GCGGAACCAT  TTGGTAGCCA  AGTCGAGGAA      2220

CTTGAGAGCA  TGCGGCCGCT  TTTTGTGTGT  GTGTGTGTGT  GTGTGTGTGT  GTGTGTGTGT      2280

GTGTGTTTTC  CGTGTCGATC  CGAACAACCT  CATGAAAATT  TCAGGCTAAT  TCTCAAGATT      2340

CTGTCCCTTT  TCCGAAACGC  CAAATAAGGT  CGAGGTGTCC  GTTTCGGTCG  TCCCTCGAGA      2400

ACTGGTGCCA  GGCAGCTGCT  GGCGTCGGTA  GAGACGCGAG  GGTGTGTGTG  TTCTGTCTGC      2460

GTTCAATGGA  AACGGTTCTC  TTATTCAATG  GTCTTCGTTT  GG                          2502
```

(2) INFORMATION FOR SEQ ID NO: 3:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
TGTTCACCTA  CAGGGCTCAG  TTATGCTAAA  ATTAGACTTG  AAAATGAAGC  ATATGACGAA       60

GACGGAAGCT  CATTACCAGA  CTTGGCTTTT  GACAGTGATC  AGATTGCTAT  ACGAAACCCA      120

CCATCTGTAA  TTGACGATGT  GTATACATTA  TATTACCCAC  CAGAGAAGAG  AACAGAAAGG      180

CATGCTGATG  GAATATTTAA  TAAAGCCTAT  AGGAAGGTAC  TCGGTCAGTT  GTCAGCAAGA      240

AAATATCTAC  ATTCTGTGAT  GGCAAAGCGC  GTAGGAGGTG  TGAGCAGTAT  GGAGGAAGAT      300

TCAGAACCTT  TATCCAAAAG  GCACTCGGAT  CGGATCTTC                               339
```

(2) INFORMATION FOR SEQ ID NO: 4:

(i) SEQUENCE CHARACTERISTICS:
        (A) LENGTH: 312 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CACGAGCCGG  ATCCGATACA  GCGTCTATTT  CGACACTGGA  ATAGCAGGAC  AATGTCTAGT       60

AAAGCGACTT  TAGCCTTACT  CATCTCTGGA  ATCATAATGC  ACTACAGTGT  CTACTGCTCA      120

CCTCTCGGGC  TTAACTATCC  TAACCTTAGA  CTTGAAAATG  AGGTTTATGA  CGAGGATGGG      180

AATTCGTTAC  CGGCCTTGGC  TTTTGACAGC  GATCAAATTG  CTATAAGAAG  TCCCCCGTCT      240

GTGGCTGACG  ATTTGTACAC  TTTATACTAC  CCACCGGAGA  AAAGTGGAGG  GAGCACCATG      300

GAAGACGACA  CA                                                              312
```

(2) INFORMATION FOR SEQ ID NO: 5:

(i) SEQUENCE CHARACTERISTICS:
        (A) LENGTH: 305 base pairs
        (B) TYPE: nucleic acid
        (C) STRANDEDNESS: single
        (D) TOPOLOGY: linear ( i i ) MOLECULE TYPE: cDNA ( x i ) SEQUENCE DESCRIPTION: SEQ ID NO: 5:

| GCACGAGACA | GGCTTGGGTA | CTTTAGAATG | TTTGGAGCAG | GACAATGTCT | AGTAAAGCGA | 60 |
| CTTTAGCCTT | ACTCATCTCT | GGAATCATAA | TGCACTACAG | TGTCTACTGC | TCACCTCTCG | 120 |
| GGCTTAACTA | TCCTAACCTT | AGACTTGAAA | ATGAGGTTTA | TGACGAGGAT | GGGAATTCGT | 180 |
| TACCGGCCTT | GGCTTTTGAC | AGCGATCAAA | TTGCTATAAG | AAGTCCCCCG | TCTGTGGCTG | 240 |
| ACGATTTGTA | CACTTTATAC | TACCCACCGG | AGAAAAGTGG | AGGGAGCACC | ATGGAAGACG | 300 |
| ACACA | | | | | | 305 |

( 2 ) INFORMATION FOR SEQ ID NO: 6:

( i ) SEQUENCE CHARACTERISTICS:
        ( A ) LENGTH: 173 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 6:

```
Met Ser Ser Lys Ala Thr Leu Ala Leu Leu Ile Tyr Gly Ile Ile Met
 1               5                  10                  15
His Tyr Ser Val Tyr Ser Ser Pro Leu Gly Leu Asn Tyr Pro Asn Leu
                20                  25                  30
Arg Leu Glu Asn Glu Val Tyr Asp Glu Asp Gly Asn Ser Leu Pro Ala
            35                  40                  45
Leu Ala Phe Asp Ser Asp Gln Ile Ala Ile Arg Ser Pro Pro Ser Val
        50                  55                  60
Ala Asp Asp Leu Tyr Thr Leu Tyr Tyr Pro Pro Glu Lys Gly Thr Glu
65                  70                  75                  80
Arg His Ala Asp Gly Met Phe Asn Lys Ala Tyr Arg Lys Ala Leu Gly
                85                  90                  95
Gln Leu Ser Ala Arg Lys Tyr Leu His Ser Leu Met Ala Lys Arg Val
                100                 105                 110
Gly Gly Gly Ser Thr Met Glu Asp Asp Thr Glu Pro Leu Ser Lys Arg
            115                 120                 125
His Ser Asp Gly Ile Phe Thr Asp Ser Tyr Ser Arg Tyr Arg Lys Gln
        130                 135                 140
Met Ala Val Lys Lys Tyr Leu Ala Ala Val Leu Gly Lys Arg Tyr Arg
145                 150                 155                 160
Gln Arg Tyr Arg Asn Lys Gly Arg Arg Leu Gly Tyr Leu
                165                 170
```

( 2 ) INFORMATION FOR SEQ ID NO: 7:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 7:

```
Met Ala Lys Ser Ser Arg Ala Thr Leu Ala Leu Leu Ile Tyr Gly Ile
 1               5                  10                  15
Leu Met Arg Tyr Ser Gln Cys Thr Pro Ile Gly Met Gly Phe Pro Asn
```

|   |   |   | 20 |   |   |   | 25 |   |   |   | 30 |   |   |   |
|---|---|---|---|---|---|---|---|---|---|---|---|---|---|---|
| Met | Arg | Leu | Asp | Asn | Asp | Val | Phe | Gly | Asp | Glu | Gly | Asn | Ser | Leu | Ser |
|   |   | 35 |   |   |   | 40 |   |   |   | 45 |   |   |   |
| Glu | Leu | Ser | Tyr | Glu | Pro | Asp | Thr | Met | Ser | Ala | Arg | Ser | Arg | Pro | Ala |
|   | 50 |   |   |   | 55 |   |   |   | 60 |   |   |   |
| Leu | Pro | Glu | Asp | Ala | Tyr | Thr | Leu | Tyr | Tyr | Pro | Pro | Glu | Arg | Arg | Ala |
| 65 |   |   |   | 70 |   |   |   | 75 |   |   |   | 80 |
| Glu | Thr | His | Ala | Asp | Gly | Leu | Leu | Asp | Arg | Ala | Leu | Arg | Asp | Ile | Leu |
|   |   |   | 85 |   |   |   | 90 |   |   |   | 95 |
| Val | Gln | Leu | Ser | Ala | Arg | Lys | Tyr | Leu | His | Ser | Leu | Thr | Ala | Val | Arg |
|   |   | 100 |   |   |   | 105 |   |   |   | 110 |   |
| Val | Gly | Glu | Glu | Glu | Glu | Asp | Glu | Asp | Ser | Glu | Pro | Leu | Ser | Lys |
|   |   | 115 |   |   |   | 120 |   |   |   | 125 |   |   |
| Arg | His | Ser | Asp | Gly | Ile | Phe | Thr | Asp | Ser | Tyr | Ser | Arg | Tyr | Arg | Lys |
|   | 130 |   |   |   | 135 |   |   |   | 140 |
| Gln | Met | Ala | Val | Lys | Lys | Ile | Pro | Cys | Ser | Ser | Ala | Gly | Lys | Lys | Val |
| 145 |   |   |   | 150 |   |   |   | 155 |   |   |   | 160 |
| Gln | Thr | Glu | Arg | Ala | Ala | Asn | Ser | Arg | Arg | Ile | Gly | Cys | Thr | Ile | Ser |
|   |   |   | 165 |   |   |   | 170 |   |   |   | 175 |
| Leu | Asp | Gly | His |
|   |   |   | 180 |

(2) INFORMATION FOR SEQ ID NO: 8:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

| His | Ala | Asp | Gly | Met | Phe | Asn | Lys | Ala | Tyr | Arg | Lys | Ala | Leu | Gly | Gln |
|---|---|---|---|---|---|---|---|---|---|---|---|---|---|---|---|
| 1 |   |   |   | 5 |   |   |   | 10 |   |   |   | 15 |
| Leu | Ser | Ala | Arg | Lys | Tyr | Leu | His | Ser | Leu | Met | Ala | Lys | Arg | Val | Gly |
|   |   |   | 20 |   |   |   | 25 |   |   |   | 30 |
| Gly | Gly | Ser | Thr | Met | Glu | Asp | Asp | Thr | Glu | Pro | Leu | Ser |
|   |   |   | 35 |   |   |   | 40 |   |   |   | 45 |

(2) INFORMATION FOR SEQ ID NO: 9:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

| His | Ser | Asp | Gly | Ile | Phe | Thr | Asp | Ser | Tyr | Ser | Arg | Tyr | Arg | Lys | Gln |
|---|---|---|---|---|---|---|---|---|---|---|---|---|---|---|---|
| 1 |   |   |   | 5 |   |   |   | 10 |   |   |   | 15 |
| Met | Ala | Val | Lys | Lys | Tyr | Leu | Ala | Ala | Val | Leu | Gly | Lys | Arg | Tyr | Arg |
|   |   |   | 20 |   |   |   | 25 |   |   |   | 30 |
| Gln | Arg | Tyr | Arg | Asn | Lys |
|   |   |   | 35 |

(2) INFORMATION FOR SEQ ID NO: 10:

(i) SEQUENCE CHARACTERISTICS:

(A) LENGTH: 87 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 10:

```
Met Ser Ser Lys Ala Thr Leu Ala Leu Leu Ile Tyr Gly Ile Ile Met
 1               5                  10                  15
His Tyr Ser Ile Tyr Cys Ser Pro Leu Gly Leu Asn Tyr Pro Asn Leu
            20                  25                  30
Arg Leu Glu Asn Glu Val Tyr Asp Glu Asp Gly Asn Ser Leu Pro Ala
         35                  40                  45
Phe Gly Phe Asp Ser Asp Gln Ile Ala Ile Arg Ser Pro Pro Ser Val
     50                  55                  60
Ala Asp Asp Leu Tyr Thr Leu Tyr Tyr Pro Pro Glu Lys Ser Gly Gly
 65                  70                  75                  80
Ser Thr Met Glu Asp Asp Thr
                 85
```

(2) INFORMATION FOR SEQ ID NO: 11:

(i) SEQUENCE CHARACTERISTICS:
(A) LENGTH: 113 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 11:

```
Cys Ser Pro Thr Gly Leu Ser Tyr Ala Lys Ile Arg Leu Glu Asn Glu
 1               5                  10                  15
Ala Tyr Asp Glu Asp Gly Ser Ser Leu Pro Asp Leu Ala Phe Asp Ser
            20                  25                  30
Asp Gln Ile Ala Ile Arg Asn Pro Pro Ser Val Ile Asp Asp Val Tyr
         35                  40                  45
Thr Leu Tyr Tyr Pro Pro Glu Lys Arg Thr Glu Arg His Ala Asp Gly
     50                  55                  60
Ile Phe Asn Lys Ala Tyr Arg Lys Val Leu Gly Gln Leu Ser Ala Arg
 65                  70                  75                  80
Lys Tyr Leu His Ser Val Met Ala Lys Arg Val Gly Gly Val Ser Ser
            85                  90                  95
Met Glu Glu Asp Ser Glu Pro Leu Ser Lys Arg His Ser Asp Arg Ile
            100                 105                 110
Phe
```

(2) INFORMATION FOR SEQ ID NO: 12:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 12:

```
CATCGCGACT GGATGTTTCA A                                      21
```

(2) INFORMATION FOR SEQ ID NO: 13:

(i) SEQUENCE CHARACTERISTICS:

( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

GGAATCATAA TGCACTACAG TGTC					24

( 2 ) INFORMATION FOR SEQ ID NO: 14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

TGACAGAGGC TCTGTGTC					18

( 2 ) INFORMATION FOR SEQ ID NO: 15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

TCGGTAGCGG CTGTAGCTAT CTG					23

( 2 ) INFORMATION FOR SEQ ID NO: 16:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

CTACACGCTT TGCCATCAGA GA					22

( 2 ) INFORMATION FOR SEQ ID NO: 17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

GAACACAAGA GCGATCCACT GA					22

( 2 ) INFORMATION FOR SEQ ID NO: 18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

GGCTCGAGCC CGGGAATTCC G					21

( 2 ) INFORMATION FOR SEQ ID NO: 19:

( i ) SEQUENCE CHARACTERISTICS:
        ( A ) LENGTH: 21 base pairs
        ( B ) TYPE: nucleic acid

```
        ( C ) STRANDEDNESS: single
        ( D ) TOPOLOGY: linear ( x i ) SEQUENCE DESCRIPTION: SEQ ID NO: 19:

GGCTCGAGCC  CGGGAATTCC  G                                                        21

( 2 ) INFORMATION FOR SEQ ID NO:20:

( i ) SEQUENCE CHARACTERISTICS:
        ( A ) LENGTH: 176 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Met  Thr  Met  Cys  Ser  Gly  Ala  Arg  Leu  Ala  Leu  Leu  Val  Tyr  Gly  Ile
 1              5                        10                       15

Ile  Met  His  Ser  Ser  Val  Tyr  Ser  Ser  Pro  Ala  Ala  Ala  Gly  Leu  Arg
              20                        25                       30

Phe  Pro  Gly  Ile  Arg  Pro  Glu  Glu  Glu  Ala  Tyr  Gly  Glu  Asp  Gly  Asn
              35                        40                       45

Pro  Leu  Pro  Asp  Phe  Gly  Gly  Ser  Glu  Pro  Pro  Gly  Ala  Gly  Ser  Pro
         50                        55                       60

Ala  Ser  Ala  Pro  Arg  Ala  Ala  Ala  Trp  Tyr  Arg  Pro  Ala  Gly  Arg
 65                       70                        75                       80

Arg  Asp  Val  Ala  His  Gly  Ile  Leu  Asn  Glu  Ala  Tyr  Arg  Lys  Val  Leu
                   85                        90                       95

Asp  Gln  Leu  Ser  Ala  Gly  Lys  His  Leu  Gln  Ser  Leu  Val  Ala  Arg  Gly
             100                       105                      110

Val  Gly  Gly  Ser  Leu  Gly  Gly  Gly  Ala  Gly  Asp  Asp  Ala  Glu  Pro  Leu
             115                       120                      125

Ser  Lys  Arg  His  Ser  Asp  Gly  Ile  Phe  Thr  Asp  Ser  Tyr  Ser  Arg  Tyr
     130                       135                      140

Arg  Lys  Gln  Met  Ala  Val  Lys  Lys  Tyr  Leu  Ala  Ala  Val  Leu  Gly  Lys
145                       150                      155                      160

Arg  Tyr  Lys  Gln  Arg  Val  Lys  Asn  Lys  Gly  Arg  Arg  Ile  Ala  Tyr  Leu
                  165                       170                      175

( 2 ) INFORMATION FOR SEQ ID NO:21:

( i ) SEQUENCE CHARACTERISTICS:
        ( A ) LENGTH: 176 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Met  Thr  Met  Cys  Ser  Gly  Ala  Arg  Leu  Ala  Leu  Leu  Val  Tyr  Gly  Ile
 1              5                        10                       15

Leu  Met  His  Ser  Ser  Val  Tyr  Gly  Ser  Pro  Ala  Ala  Ser  Gly  Leu  Arg
              20                        25                       30

Phe  Pro  Gly  Ile  Arg  Pro  Glu  Asn  Glu  Ala  Tyr  Asp  Glu  Asp  Gly  Asn
              35                        40                       45

Pro  Gln  Gln  Asp  Phe  Tyr  Asp  Ser  Glu  Pro  Pro  Gly  Val  Gly  Ser  Pro
         50                        55                       60

Ala  Ser  Ala  Leu  Arg  Asp  Ala  Ala  Ala  Leu  Tyr  Tyr  Pro  Ala  Glu  Glu
 65                       70                        75                       80
```

```
Arg  Asp  Val  Ala  His  Gly  Ile  Leu  Asp  Lys  Ala  Tyr  Arg  Lys  Val  Leu
                    85                  90                       95

Asp  Gln  Leu  Ser  Ala  Arg  Arg  Tyr  Leu  Gln  Thr  Leu  Met  Ala  Lys  Gly
               100                      105                      110

Leu  Gly  Gly  Thr  Pro  Gly  Gly  Gly  Ala  Asp  Asp  Asp  Ser  Glu  Pro  Leu
          115                      120                      125

Ser  Lys  Arg  His  Ser  Asp  Gly  Ile  Phe  Thr  Asp  Ser  Tyr  Ser  Arg  Tyr
     130                      135                      140

Arg  Lys  Gln  Met  Ala  Val  Lys  Lys  Tyr  Leu  Ala  Ala  Val  Leu  Gly  Lys
145                      150                      155                      160

Arg  Tyr  Lys  Gln  Arg  Val  Lys  Asn  Lys  Gly  Arg  Arg  Ile  Pro  Tyr  Leu
                    165                      170                      175
```

( 2 ) INFORMATION FOR SEQ ID NO:22:

( i ) SEQUENCE CHARACTERISTICS:
       ( A ) LENGTH: 175 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:22:

```
Met  Thr  Met  Cys  Ser  Gly  Ala  Arg  Leu  Ala  Leu  Leu  Val  Tyr  Gly  Ile
1               5                        10                      15

Ile  Met  His  Asn  Ser  Val  Ser  Cys  Ser  Pro  Ala  Ala  Gly  Leu  Ser  Phe
               20                       25                       30

Pro  Gly  Ile  Arg  Pro  Glu  Glu  Ala  Tyr  Asp  Gln  Asp  Gly  Asn  Pro
          35                       40                       45

Leu  Gln  Asp  Phe  Tyr  Asp  Trp  Asp  Pro  Pro  Gly  Ala  Gly  Ser  Pro  Ala
     50                       55                       60

Ser  Ala  Leu  Arg  Asp  Ala  Tyr  Ala  Leu  Tyr  Tyr  Pro  Ala  Asp  Arg  Arg
65                       70                       75                       80

Asp  Val  Ala  His  Glu  Ile  Leu  Asn  Glu  Ala  Tyr  Arg  Lys  Val  Leu  Asp
                    85                       90                       95

Gln  Leu  Ser  Ala  Arg  Lys  Tyr  Leu  Gln  Ser  Met  Val  Ala  Arg  Gly  Met
               100                      105                      110

Gly  Glu  Asn  Leu  Ala  Ala  Ala  Ala  Val  Asp  Asp  Arg  Ala  Pro  Leu  Thr
          115                      120                      125

Lys  Arg  His  Ser  Asp  Gly  Ile  Phe  Thr  Asp  Ser  Tyr  Ser  Arg  Tyr  Arg
     130                      135                      140

Lys  Gln  Met  Ala  Val  Lys  Lys  Tyr  Leu  Ala  Ala  Val  Leu  Gly  Lys  Arg
145                      150                      155                      160

Tyr  Lys  Gln  Arg  Val  Lys  Asn  Lys  Gly  Arg  Arg  Ile  Ala  Tyr  Leu
                    165                      170                      175
```

( 2 ) INFORMATION FOR SEQ ID NO:23:

( i ) SEQUENCE CHARACTERISTICS:
       ( A ) LENGTH: 45 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:23:

```
His  Ala  Asp  Gly  Met  Phe  Asn  Lys  Ala  Tyr  Arg  Lys  Ala  Leu  Gly  Gln
1               5                        10                      15
```

```
        Leu  Ser  Ala  Arg  Lys  Tyr  Leu  His  Thr  Leu  Met  Ala  Lys  Arg  Val  Gly
                       20                  25                       30

Gly  Gly  Ser  Met  Ile  Glu  Asp  Asp  Asn  Glu  Pro  Leu  Ser
                       35                  40                       45
```

( 2 ) INFORMATION FOR SEQ ID NO:24:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
        His  Ala  Asp  Gly  Leu  Leu  Asp  Arg  Ala  Leu  Arg  Asp  Ile  Leu  Val  Gln
        1                   5                        10                       15

Leu  Ser  Ala  Arg  Lys  Tyr  Leu  His  Ser  Leu  Thr  Ala  Val  Arg  Val  Gly
                       20                  25                       30

Glu  Glu  Glu  Glu  Asp  Glu  Glu  Asp  Ser  Glu  Pro  Leu  Ser
                       35                  40                       45
```

( 2 ) INFORMATION FOR SEQ ID NO:25:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
        His  Ala  Asp  Gly  Ile  Phe  Asn  Lys  Ala  Tyr  Arg  Lys  Val  Leu  Gly  Gln
        1                   5                        10                       15

Leu  Ser  Ala  Arg  Lys  Tyr  Leu  His  Ser  Val  Met  Ala  Lys  Arg  Val  Gly
                       20                  25                       30

Gly  Val  Ser  Ser  Met  Glu  Glu  Asp  Ser  Glu  Pro  Leu  Ser
                       35                  40                       45
```

( 2 ) INFORMATION FOR SEQ ID NO:26:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
        His  Val  Asp  Ala  Ile  Phe  Thr  Thr  Asn  Tyr  Arg  Lys  Leu  Leu  Ser  Gln
        1                   5                        10                       15

Leu  Tyr  Ala  Arg  Lys  Val  Ile  Gln  Asp  Ile  Met  Asn  Lys  Gln  Gly  Glu
                       20                  25                       30

Arg  Ile  Gln  Glu  Gln  Arg  Ala  Arg  Leu  Ser
                       35                  40
```

( 2 ) INFORMATION FOR SEQ ID NO:27:

( i ) SEQUENCE CHARACTERISTICS:
        ( A ) LENGTH: 43 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:27:

```
His Ala Asp Ala Ile Phe Thr Ser Ser Tyr Arg Arg Ile Leu Gly Gln
 1               5                  10                  15
Leu Tyr Ala Arg Lys Leu Leu His Glu Ile Met Asn Arg Gln Gln Gly
            20                  25                  30
Glu Arg Asn Gln Glu Gln Arg Ser Arg Phe Asn
            35                  40
```

(2) INFORMATION FOR SEQ ID NO:28:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Tyr Ala Asp Ala Ile Phe Thr Asn Ser Tyr Arg Lys Ile Leu Gly Gln
 1               5                  10                  15
Leu Ser Ala Arg Lys Leu Leu Gln Asp Ile Met Asn Arg Gln Gln Gly
            20                  25                  30
Glu Arg Asn Gln Glu Gln Gly Ala Lys Val Arg Leu
            35                  40
```

(2) INFORMATION FOR SEQ ID NO:29:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

```
Tyr Ala Asp Ala Ile Phe Thr Asn Ser Tyr Arg Lys Val Leu Gly Gln
 1               5                  10                  15
Leu Ser Ala Arg Lys Leu Leu Gln Asp Ile Met Asn Arg Gln Gln Gly
            20                  25                  30
Glu Arg Asn Gln Glu Gln Gly Ala Lys Val Arg Leu
            35                  40
```

(2) INFORMATION FOR SEQ ID NO:30:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

```
Tyr Ala Asp Ala Ile Phe Thr Asn Ser Tyr Arg Lys Val Leu Gly Gln
 1               5                  10                  15
Leu Ser Ala Arg Lys Leu Leu Gln Asp Ile Met Asn Arg Gln Gln Gly
            20                  25                  30
Glu Arg Asn Gln Glu Gln Gly Ala Lys Val Arg Leu
            35                  40
```

(2) INFORMATION FOR SEQ ID NO:31:

(i) SEQUENCE CHARACTERISTICS:
　　　　(A) LENGTH: 44 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:31:

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Arg Asn Gln Glu Gln Gly Ala Arg Val Arg Leu
        35                  40

(2) INFORMATION FOR SEQ ID NO:32:

(i) SEQUENCE CHARACTERISTICS:
　　　　(A) LENGTH: 44 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO:32:

Tyr Ala Asp Ala Ile Phe Thr Asn Ser Tyr Arg Lys Val Leu Gly Gln
 1               5                  10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

(2) INFORMATION FOR SEQ ID NO:33:

(i) SEQUENCE CHARACTERISTICS:
　　　　(A) LENGTH: 146 base pairs
　　　　(B) TYPE: nucleic acid
　　　　(C) STRANDEDNESS: single
　　　　(D) TOPOLOGY: linear (xi) SEQUENCE DESCRIPTION: SEQ ID NO:33:

CGTTGCTAAC CCAAACTACC ATGTGTGTAC AGCCCAGATC AAGTCATTTT GAGATAACTG　　60

AACAATCAAT CAGTGGATCG CTCTTGTGTT CTTTAAACAT GTATTTATGT ATGAAGTAAA　120

GCCATTAAAA TGAATATTTT GATAAT　　　　　　　　　　　　　　　　　　　　146

(2) INFORMATION FOR SEQ ID NO:34:

(i) SEQUENCE CHARACTERISTICS:
　　　　(A) LENGTH: 147 base pairs
　　　　(B) TYPE: nucleic acid
　　　　(C) STRANDEDNESS: single
　　　　(D) TOPOLOGY: linear (xi) SEQUENCE DESCRIPTION: SEQ ID NO:34:

CGATGGGTTA CCAGCTACCC TGTGTATACA GCCCTGACGC AATGAAAAGT CGTTTTCCAA　　60

ACTGACTCAA CAGTCATCGC TCGTGTGTTC TATCCAAACA TGTATTTATG TAATGAAGTA　120

AAGCCATTAA ATGAATATTT TGATAAT　　　　　　　　　　　　　　　　　　　147

(2) INFORMATION FOR SEQ ID NO:35:

(i) SEQUENCE CHARACTERISTICS:
      (A) LENGTH: 145 base pairs
      (B) TYPE: nucleic acid
      (C) STRANDEDNESS: single
      (D) TOPOLOGY: linear (xi) SEQUENCE DESCRIPTION: SEQ ID NO:35:

```
CGACGAGTTA CCAGCTATCC TGTGTATACA GCCCTGACAC AATGAGAAGT CGTTTTCCCA      60
ACTGACTGAA CTGTCATCGC TGCTGTGTTC TGTCCCACAT GTATTTATGT ATGAAGTCAA     120
GCCATTAAAT GAATATTTTG ATAAT                                           145
```

(2) INFORMATION FOR SEQ ID NO:36:

(i) SEQUENCE CHARACTERISTICS:
      (A) LENGTH: 135 base pairs
      (B) TYPE: nucleic acid
      (C) STRANDEDNESS: single
      (D) TOPOLOGY: linear (xi) SEQUENCE DESCRIPTION: SEQ ID NO:36:

```
CGATGAGTTG CCAGCTACCG TGTGTATAAA ATGAAAAGTC GTTTTCCAAA TTGACTGACC      60
AGTCATCACT CATGTGTTCT TTCCAAACAT GTATTTATGT ATCAAGTAAA GCCATTAAAT     120
GACTATTTTG ATAAT                                                      135
```

(2) INFORMATION FOR SEQ ID NO:37:

(i) SEQUENCE CHARACTERISTICS:
      (A) LENGTH: 27 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:37:

```
His Ala Asp Gly Val Phe Thr Ser Asp Phe Ser Lys Leu Leu Gly Gln
 1               5                  10                  15
Leu Ser Ala Lys Lys Tyr Leu Glu Ser Leu Met
                20                  25
```

(2) INFORMATION FOR SEQ ID NO:38:

(i) SEQUENCE CHARACTERISTICS:
      (A) LENGTH: 27 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:38:

```
His Ala Asp Gly Val Phe Thr Ser Asp Tyr Ser Arg Leu Leu Gly Gln
 1               5                  10                  15
Ile Ser Ala Lys Lys Tyr Leu Glu Ser Leu Ile
                20                  25
```

(2) INFORMATION FOR SEQ ID NO:39:

(i) SEQUENCE CHARACTERISTICS:
      (A) LENGTH: 28 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:39:

His Ser Asp Ala Val Phe Thr Asp Asn Tyr Ser Arg Ile Arg Lys Gln
1               5                   10                  15
Met Ala Val Lys Lys Tyr Ile Asn Ser Leu Leu Ala
            20                  25

(2) INFORMATION FOR SEQ ID NO:40:

(i) SEQUENCE CHARACTERISTICS:
    (A) LENGTH: 28 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:40:

His Ser Asp Ala Val Phe Thr Asp Asn Tyr Thr Arg Leu Arg Lys Gln
1               5                   10                  15
Met Ala Val Lys Lys Tyr Leu Asn Ser Ile Leu Asn
            20                  25

(2) INFORMATION FOR SEQ ID NO:41:

(i) SEQUENCE CHARACTERISTICS:
    (A) LENGTH: 29 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:41:

His Ser Glu Gly Thr Phe Ser Asn Asp Tyr Ser Lys Tyr Gln Glu Glu
1               5                   10                  15
Arg Met Ala Gln Asp Phe Val Gln Trp Leu Met Asn Ser
            20                  25

(2) INFORMATION FOR SEQ ID NO:42:

(i) SEQUENCE CHARACTERISTICS:
    (A) LENGTH: 31 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:42:

His Ala Asp Gly Thr Tyr Thr Ser Asn Val Ser Thr Tyr Leu Gln Asp
1               5                   10                  15
Gln Ala Ala Lys Asp Phe Val Ser Trp Leu Lys Ser Gly Arg Ala
            20                  25                  30

(2) INFORMATION FOR SEQ ID NO:43:

(i) SEQUENCE CHARACTERISTICS:
    (A) LENGTH: 27 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:43:

His Ser Asp Gly Thr Phe Thr Ser Glu Leu Ser Arg Leu Arg Glu Gly
1               5                   10                  15

Ala Arg Leu Gln Arg Leu Leu Gln Gly Leu Val
            20              25

(2) INFORMATION FOR SEQ ID NO:44:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

(2) INFORMATION FOR SEQ ID NO:45:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

Asp Val Ala His Gly Ile Leu Asp Lys Ala Tyr Arg Lys Val Leu Asp
1               5                   10                  15

Gln Leu Ser Ala Arg Arg Tyr Leu Gln Thr Leu Met Ala Lys Gly Leu
            20                  25                  30

Gly Gly Thr Pro Gly Gly Gly Ala Asp Asp Ser Glu Pro Leu Ser
            35              40                  45

(2) INFORMATION FOR SEQ ID NO:46:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

Asp Val Ala His Gly Ile Leu Asn Glu Ala Tyr Arg Lys Val Leu Asp
1               5                   10                  15

Gln Leu Ser Ala Gly Lys His Leu Gln Ser Leu Val Ala Arg Gly Val
            20                  25                  30

Gly Gly Ser Leu Gly Gly Gly Ala Gly Asp Asp Ala Glu Pro Leu Ser
            35              40                  45

(2) INFORMATION FOR SEQ ID NO:47:

(i) SEQUENCE CHARACTERISTICS:
        (A) LENGTH: 48 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:47:

```
Asp Val Ala His Glu Ile Leu Asn Glu Ala Tyr Arg Lys Val Leu Asp
1               5                   10                  15
Gln Leu Ser Ala Arg Lys Tyr Leu Gln Ser Met Val Ala Arg Gly Met
            20                  25                  30
Gly Glu Asn Leu Ala Ala Ala Ala Val Asp Asp Arg Ala Pro Leu Thr
            35              40                  45
```

(2) INFORMATION FOR SEQ ID NO:48:

(i) SEQUENCE CHARACTERISTICS:
 (A) LENGTH: 84 base pairs
 (B) TYPE: nucleic acid
 (C) STRANDEDNESS: single
 (D) TOPOLOGY: linear (i i) MOLECULE TYPE: cDNA (x i) SEQUENCE DESCRIPTION: SEQ ID NO:48:

CGTTTTCCT CAGTCTGACT GTGGAAATGT TAGATAGCCT TCGCACATTT AACGTTGTGA     60

TATTTCTTC CCCACAGCAG AACA     84

(2) INFORMATION FOR SEQ ID NO:49:

(i) SEQUENCE CHARACTERISTICS:
 (A) LENGTH: 39 base pairs
 (B) TYPE: nucleic acid
 (C) STRANDEDNESS: single
 (D) TOPOLOGY: linear (i i) MOLECULE TYPE: cDNA (x i) SEQUENCE DESCRIPTION: SEQ ID NO:49:

GACATCCAGC TTGTCTCTCC ACACGGTAAT AGCAGGACA     39
68